(12) United States Patent
Kohlbrenner et al.

(10) Patent No.: US 8,048,037 B2
(45) Date of Patent: Nov. 1, 2011

(54) INJECTION DEVICE COMPRISING SEVERAL COUPLING MECHANISMS

(75) Inventors: Philippe Kohlbrenner, Kaltacker (CH); Peter Stettler, Kirchberg (CH); Patrick Hostettler, Hasle-Ruegsau (CH); Juergen Wittmann, Burgdorf (CH); Martin Wittwer, Wyssachen (CH)

(73) Assignee: TecPharma Licensing AG, Brugdorf (CH)

( * ) Notice: Subject to any disclaimer, the term of this patent is extended or adjusted under 35 U.S.C. 154(b) by 40 days.

(21) Appl. No.: 12/403,887

(22) Filed: Mar. 13, 2009

(65) Prior Publication Data

US 2009/0254035 A1 Oct. 8, 2009

Related U.S. Application Data

(63) Continuation of application No. PCT/CH2007/000243, filed on May 11, 2007.

(51) Int. Cl.
*A61M 5/315* (2006.01)
*A61M 5/00* (2006.01)

(52) U.S. Cl. ........ 604/220; 604/207; 604/208; 604/211; 604/218; 604/224; 604/232

(58) Field of Classification Search .................. 604/181, 604/187, 192, 193, 207–211, 218, 220, 223, 604/224, 232
See application file for complete search history.

(56) References Cited

U.S. PATENT DOCUMENTS

| | | |
|---|---|---|
| 2,771,217 A | 11/1956 | Brown et al. |
| 3,202,151 A | 8/1965 | Kath |
| 5,049,125 A | 9/1991 | Accaries et al. |
| 5,514,097 A | 5/1996 | Knauer |
| 5,569,236 A | 10/1996 | Kriesel |
| 6,123,684 A | 9/2000 | Deboer et al. |
| 6,277,099 B1 | 8/2001 | Strowe et al. |
| 7,112,187 B2 | 9/2006 | Karlsson |
| 7,645,265 B2 | 1/2010 | Stamp |
| 2005/0022806 A1 | 2/2005 | Beaumont et al. |
| 2005/0080377 A1 | 4/2005 | Sadowski et al. |
| 2005/0197626 A1 | 9/2005 | Moberg et al. |
| 2005/0261634 A1 | 11/2005 | Karlsson |
| 2006/0153693 A1 | 7/2006 | Fiechter et al. |
| 2007/0021715 A1 | 1/2007 | Kohlbrenner et al. |
| 2007/0027430 A1 | 2/2007 | Hommann |
| 2008/0033369 A1 | 2/2008 | Kohlbrenner et al. |
| 2008/0051712 A1 | 2/2008 | Fiechter et al. |
| 2008/0051713 A1 | 2/2008 | Kohlbrenner et al. |
| 2008/0171997 A1 | 7/2008 | Kohlbrenner et al. |

(Continued)

FOREIGN PATENT DOCUMENTS

CH 617 857 A5 6/1980

(Continued)

*Primary Examiner* — Nicholas D Lucchesi
*Assistant Examiner* — Victoria P Campbell
(74) *Attorney, Agent, or Firm* — Dorsey & Whitney, LLP; David E. Bruhn, Esq.

(57) ABSTRACT

An injection device including a drive unit, a delivery unit, a dosing unit, a trigger for triggering an injection, a first coupling mechanism between the drive unit and the delivery unit, and a second coupling mechanism between the dosing unit and the drive unit, wherein the drive unit is tensioned by a rotation of the dosing unit and when the drive unit is tensioned the first coupling mechanism is disengaged and the second coupling mechanism is engaged, and wherein when an injection is triggered first the first coupling mechanism is engaged and then the second coupling mechanism is disengaged. In some embodiments, the device may include a third coupling mechanism which only releases the delivery unit after the engagement and disengagement which follow a triggering.

16 Claims, 20 Drawing Sheets

U.S. PATENT DOCUMENTS

| | | |
|---|---|---|
| 2008/0306445 A1 | 12/2008 | Burren et al. |
| 2009/0048561 A1 | 2/2009 | Burren et al. |
| 2009/0247959 A1 | 10/2009 | Kohlbrenner et al. |
| 2009/0247960 A1 | 10/2009 | Kohlbrenner et al. |
| 2009/0254035 A1 | 10/2009 | Kohlbrenner et al. |
| 2009/0254044 A1 | 10/2009 | Kohlbrenner et al. |

FOREIGN PATENT DOCUMENTS

| | | |
|---|---|---|
| DE | 102 29 122 | 2/2004 |
| DE | 10 2004 063 647 | 7/2006 |
| DE | 10 2004 063644 A1 | 7/2006 |
| EP | 0 554 995 A1 | 8/1993 |
| EP | 1 516 638 A1 | 3/2005 |
| EP | 1 681 070 A1 | 7/2006 |
| WO | 00/41754 A1 | 7/2000 |
| WO | 01/19434 A1 | 3/2001 |
| WO | WO 02/053214 | 7/2002 |
| WO | WO 2004/002556 | 1/2004 |
| WO | WO 2004/089450 | 10/2004 |
| WO | 2006/039930 A1 | 4/2006 |
| WO | WO 2006/130100 | 12/2006 |

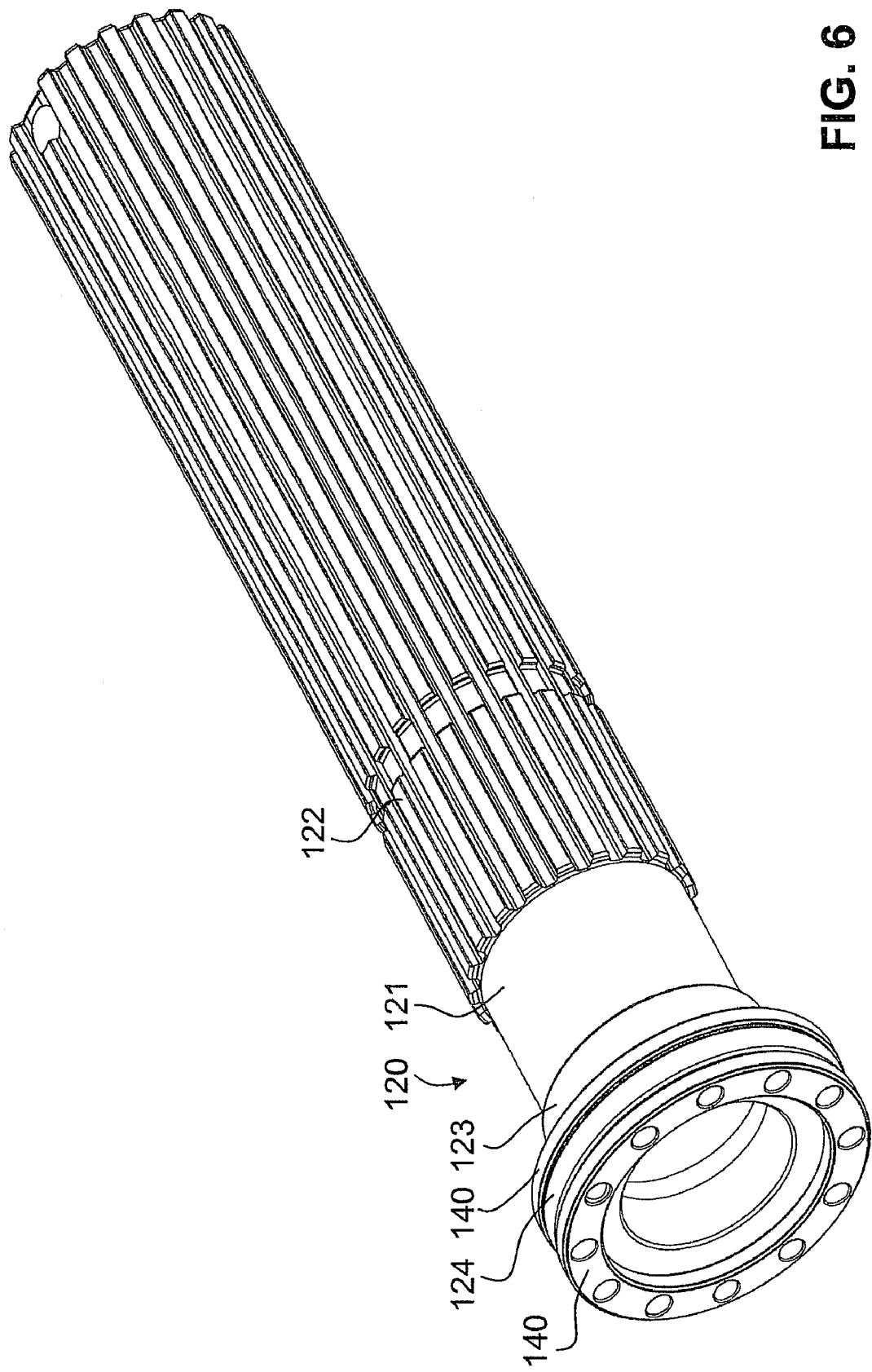

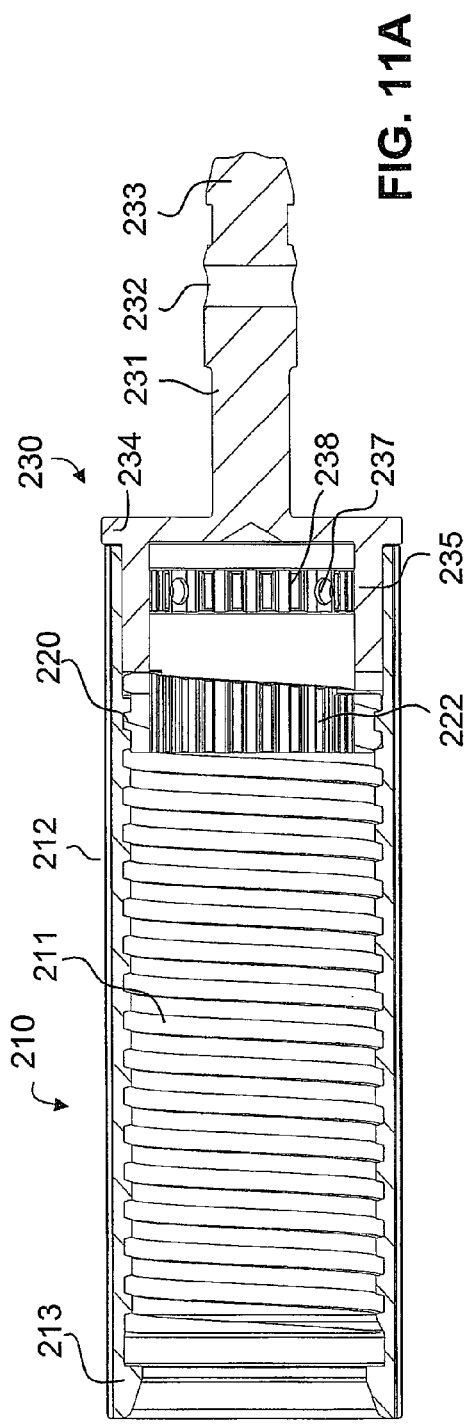
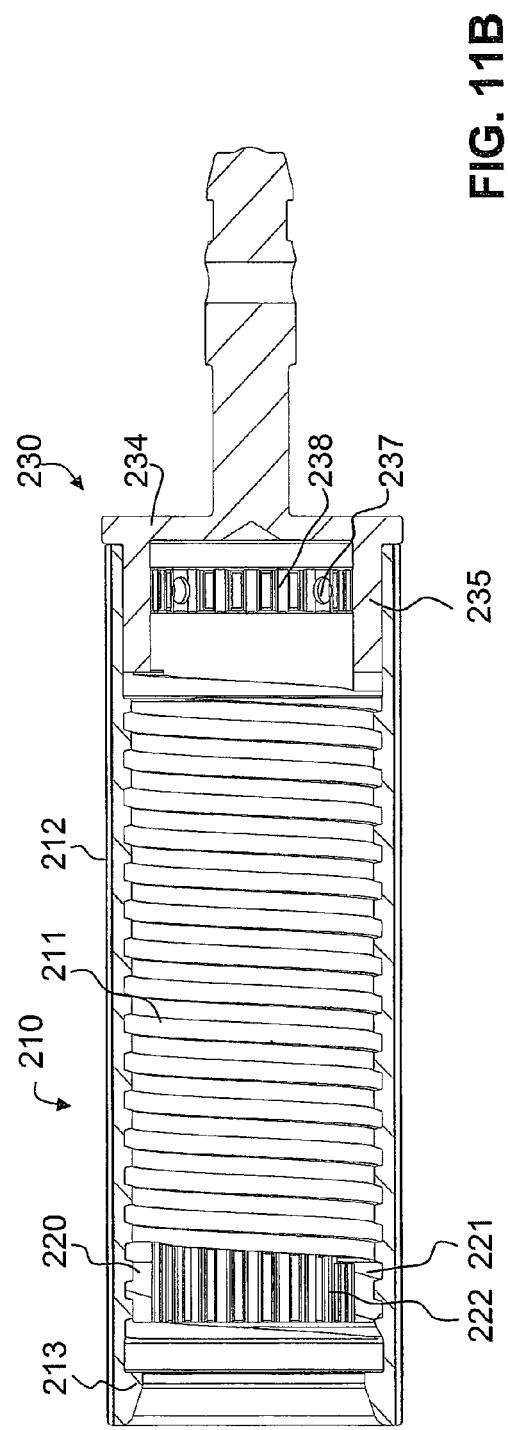
FIG. 11A
FIG. 11B

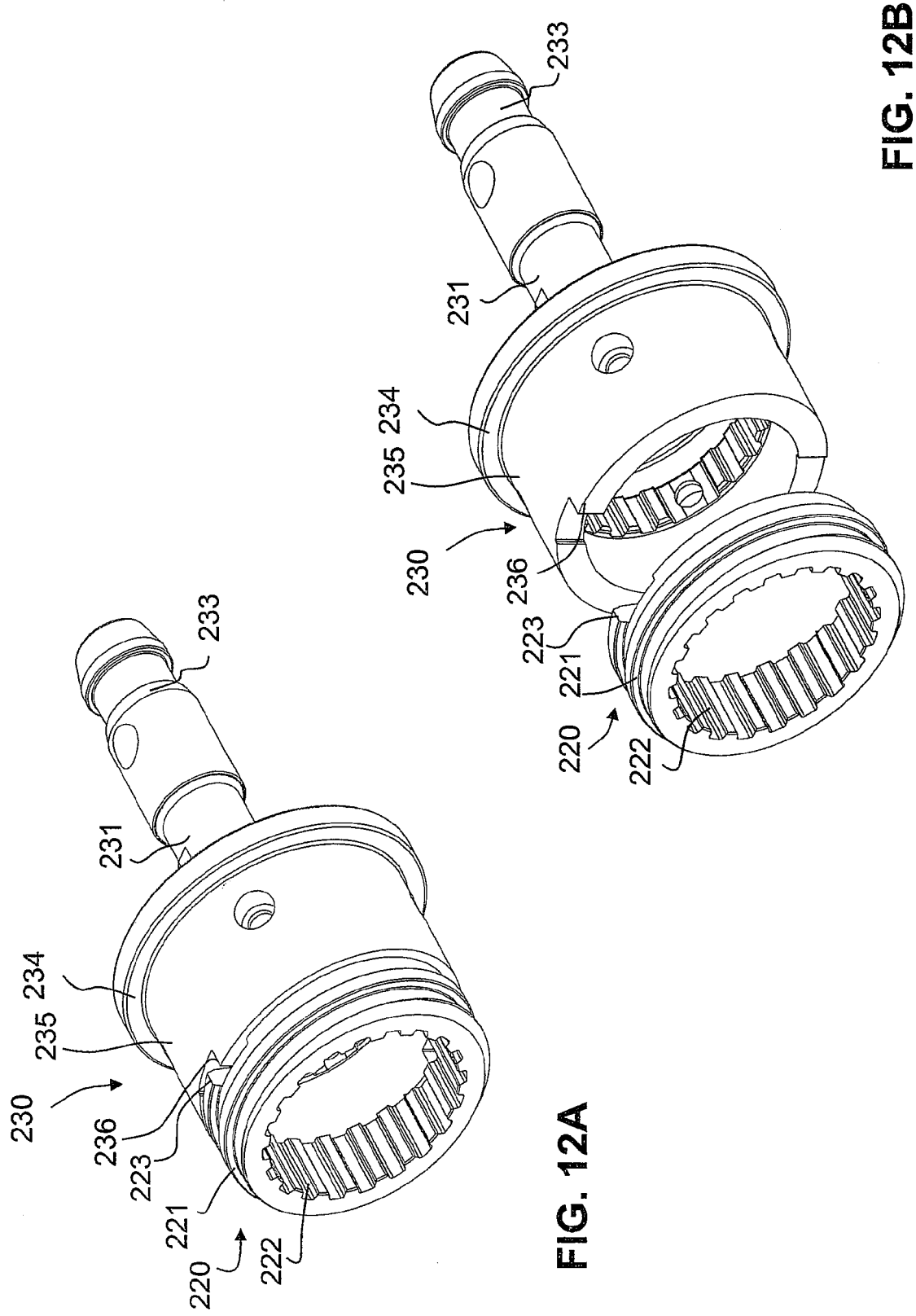

INJECTION DEVICE COMPRISING SEVERAL COUPLING MECHANISMS

CROSS-REFERENCED RELATED APPLICATIONS

This application is a continuation of International Patent Application No. PCT/CH2007/000243 filed May 11, 2007, which claims priority to Swiss Patent Application No. 1475/06 filed Sep. 15, 2006, the entire contents of both of which are incorporated herein by reference.

BACKGROUND

The present invention relates to devices for administering, injecting, delivering, infusing or dispensing a substance, and to methods of making and using such devices. More particularly, it relates to such a device for delivering a fluid product, wherein the device can be developed as an injection device for the injection of an adjustable dose of the product and can take the form of an injection pen, i.e. a compact injection device in pen-like form.

A large number of injection devices are known from the prior art for the dosed administering of medicaments or therapeutic agents such as insulin, growth hormones or osteoporosis drugs, which must be administered regularly. Such devices are on one hand intended to reliably and precisely deliver a dose which is able to be pre-set. On the other hand, they are intended to be user-friendly to a high degree. This applies all the more because they are generally operated by a person for self-administration.

The medicament can be housed in an exchangeable carpule (which also may be thought of and/or referred to as an ampoule, receptacle, container or reservoir), which is able to be inserted into a carpule holder. The latter can then be associated with or fastened to a housing of the injection device, e.g. by a screw connection or a bayonet connection. For distribution, a product stopper or piston in the carpule is pushed forward (toward the needle associated with the injection device) by a delivery arrangement with a delivery element in the form of a piston rod.

Compact, pen-shaped administering devices are known, in which the distribution takes place automatically after a first triggering (e.g. "power-assisted pens"). The dose in such devices is generally pre-set by a rotation of a dosing button. A drive is present in the device, e.g. a spring drive, which is tensioned on setting of the dose. The device is triggered by pressing a triggering arrangement, which can be identical to the dosing button. In so doing, the drive generates a drive movement, e.g. in the form of a rotary movement, which is converted into an advancing movement of the piston rod. In the case of a drive by a rotary movement, the piston rod may be constructed as a threaded rod on which a drive nut runs.

Injection pens are disclosed in DE-A 10 2004 063 644. These comprise a housing with a reservoir for the product and a delivery arrangement for delivering the product. The delivery arrangement is able to be driven by a drive arrangement. In one embodiment, the drive arrangement has a torsion spring and a coupling input member which is able to be driven rotatably thereby, which is able to be coupled with a coupling output member of the delivery arrangement. A triggering element, which at the same time also serves as a dosing member, is connected with the drive arrangement so that the drive arrangement is tensioned by a rotation of the triggering element. With this tensioning movement, the coupling which is formed by the coupling input member and the coupling output member is uncoupled, i.e. the tensioning movement is only transferred to the drive arrangement, but not to the delivery arrangement. On tensioning, the drive arrangement is prevented from turning back relative to the housing by a ratchet connection with an element which is fixed to the housing. By axial pressing in of the triggering element, firstly the connection between the triggering element and the drive arrangement is released, so that the triggering element can idle. Then the coupling is coupled and a connection is thus produced between the drive arrangement and the delivery arrangement. Finally, the ratchet connection between the drive arrangement and the housing is released, so that the drive arrangement can now carry out a rotation and can thereby drive the delivery arrangement.

A disadvantage in the preceding arrangement is that when the triggering element is not pressed in completely, only the connection between the triggering element and the drive arrangement is released, without, however, an administering being triggered. This is an undefined operating state. In this state, the user can turn the triggering element, which in fact at the same time also serves as dosing member, without this having any influence on the administering. Such an undefined state can lead to operating errors; such a state is therefore to be avoided. Furthermore, three operations or operational phases are necessary to trigger an administering: (a) releasing of the triggering and dosing element; (b) coupling of the coupling for the connecting of drive arrangement and delivery arrangement; and (c) releasing of the ratchet connection between drive arrangement and housing. None of these phases can be omitted without destroying the functionality of the device. In actual terms, even further connections are produced and released in the known injection device. Accordingly, this requires a relatively complicated structure.

SUMMARY

It is, therefore, an object of the present invention to provide an injection device which has a simpler structure and a simplified movement and/or operational sequence on the triggering of an injection. A further object is to provide an injection device in which undefined operating states of the abovementioned type are avoided.

In one embodiment, the present invention comprises an injection device comprising a drive unit, a delivery unit, a dosing unit, a trigger for triggering an injection, a first coupling mechanism between the drive unit and the delivery unit, and a second coupling mechanism between the dosing unit and the drive unit, wherein the drive unit is tensioned by a rotation of the dosing unit and when the drive unit is tensioned the first coupling mechanism is disengaged and the second coupling mechanism is engaged, and wherein when an injection is triggered first the first coupling mechanism is engaged and then the second coupling mechanism is disengaged. In some embodiments, the injection device may comprise a third coupling mechanism which only releases the delivery unit after the engagement and disengagement which follow a triggering.

In one embodiment the present invention comprises an injection device comprising a first coupling mechanism between a drive unit and a delivery unit and a second coupling mechanism between a dosing unit and the drive unit. The drive unit is tensioned by the rotation of the dosing unit. The dosing unit is fixed in relation to the housing by a double slip coupling. When the drive unit is tensioned, the first coupling mechanism is disengaged and the second coupling mechanism is engaged. A trigger device triggers the administration process. Upon triggering, first the first coupling mechanism is engaged and the second coupling mechanism is then disengaged. The injection device can optionally be provided with a third coupling mechanism which only releases the delivery unit after said engagement and disengagement.

In one embodiment, the present invention comprises a device for administering a fluid product which has the following units: a housing, a delivery arrangement for delivering the product from a reservoir, wherein the delivery arrangement comprises a rotatable input member and a delivery element movable along a thrust axis, which delivery element is able to be driven, e.g. advanced linearly, due to a rotation of the input member, a drive arrangement for producing a drive rotational movement about the thrust axis relative to the housing, wherein the drive arrangement is able to be tensioned by a tensioning rotational movement, a rotatable dosing arrangement for setting a dose of the product which is to be administered and for tensioning the drive arrangement, and a triggering arrangement moveable from a position of rest into a triggering position for triggering an administering.

In some embodiments, the device comprises two couplings, each of which can assume a coupled (or operably connected or joined) and an uncoupled (or operably disconnected) position. A first coupling is formed between the drive arrangement and the input member of the delivery arrangement. In a coupled position of this coupling, the drive arrangement and the input member of the delivery arrangement are connected with each other so as to be locked against relative rotation, whereas in an uncoupled position these parts are detached from each other. A second coupling is formed between the dosing arrangement and the drive arrangement. In a coupled position of this coupling, the dosing arrangement and the drive arrangement are connected with each other so as to be locked against relative rotation and in an uncoupled position they are detached from each other.

In some embodiments, the couplings are operable by the triggering arrangement. In the position of rest of the triggering arrangement, the first coupling assumes its uncoupled position and the second coupling its coupled position. In this way, a rotation of the dosing arrangement is able to be transmitted to the drive arrangement, but not to the delivery arrangement. Thereby, a tensioning of the drive arrangement is made possible by a rotation of the dosing arrangement without, in so doing, the delivery arrangement being moved. The dosing arrangement is able to be fixed detachably so as to be secure with regard to torque with respect to the housing, e.g. by a ratchet connection, i.e. an elastically detachable detent connection in at least one direction (the dosing direction) by rotation of the dosing arrangement, which detent connection engages in several predefined angle positions.

A movement of the triggering arrangement from the position of rest into the triggering position thereafter brings about, first, a coupling of the first coupling and, thereafter or simultaneously, an uncoupling of the second coupling. The coupling of the first coupling causes the drive arrangement to be coupled with the delivery arrangement. However, no drive movement is possible yet, because the drive arrangement is still held by the second coupling by the dosing arrangement. Only after the second coupling is uncoupled is the drive arrangement released, and the resulting drive movement is able to be transmitted to the delivery arrangement.

The coupling arrangements therefore make possible a defined interaction of the dosing arrangement, the drive arrangement and the delivery arrangement. By the first coupling being firstly coupled and the second coupling only then being released, undefined operating states, in which one of the arrangements is rotatable without this having any effect on the operation of the device, are avoided or minimized.

Furthermore, the movement sequences are simplified, because in only two movement phases are involved to trigger an administering.

In some preferred embodiments, wherein the dosing arrangement is able to be fixed by a ratchet connection relative to the housing, this is constructed as a double slip coupling which makes possible a manual rotation of the dosing arrangement relative to the housing both in a first direction of rotation to increase the dose which is to be administered and also in an opposite direction of rotation, to reduce the dose. In this way, a simple dose correction is possible. For this, the ratchet connection has a spring-loaded toothing or element with teeth between an element which is locked against relative rotation with respect to the dosing arrangement and an element which is locked against relative rotation with respect to the housing. As the toothed area or teeth must absorb the torque of the drive arrangement in the tensioned state of the injection device, it, and/or the individual teeth comprising the toothing, is formed asymmetrically, so that for a detachment of the ratchet connection on turning back the dosing arrangement contrary to the dosing direction a greater torque is necessary than for a releasing of the connection in the dosing direction. As a whole, it can thus be achieved that the user of the injection device, when increasing the dose and in the case of a dose correction, must apply a comparable torque.

In one embodiment, the ratchet connection is formed by an axial toothing of two ratchet elements, i.e. the ratchet connection comprises two ratchet elements which are axially opposite each other, on the end faces of which teeth are constructed. A first of the ratchet elements can be formed as an axially movable ratchet ring which is spring-loaded in the direction of the second ratchet element, the ratchet ring being arranged so as to be locked against relative rotation with respect to the dosing element, and the second ratchet element can be connected so as to be locked against relative rotation and displacement with respect to the housing. To save space, the ratchet ring can be spring-loaded by a plurality of springs arranged along the periphery of the ratchet ring. A smaller space requirement thereby results than in an embodiment in which the ratchet ring is spring-loaded, for example by a helical spring extending around the thrust axis.

In some embodiments, an optional third coupling can be provided. This is constructed between the housing and the delivery arrangement. In a coupled position, the delivery arrangement is connected so as to be locked against relative rotation with respect to the housing (directly or via an element which is locked against relative rotation with respect to the housing). Thereby, the third coupling in the coupled position prevents any rotary movement of the delivery arrangement and an unintentional administering of the product which is caused thereby. In an uncoupled position, on the other hand, the delivery arrangement and the housing are detached from each other, so that in this position a movement of the delivery arrangement and thus an administering of the product becomes possible. In the position of rest of the triggering arrangement, the third coupling assumes its coupled position and thus prevents an unintentional movement of the delivery arrangement. A movement of the triggering arrangement from the position of rest into the triggering position firstly brings about a coupling of the first coupling, thereafter an uncoupling of the second coupling and finally an uncoupling of the third coupling. Thereby, the third coupling constitutes an effective security against an unintentional administering, which is only released when the device is otherwise ready to bring about an administering or make an injection.

In some preferred embodiments, an administering (or delivery or injection) takes place by the triggering arrangement being pushed axially with respect to the housing in a distal (forward) direction. For this, the triggering arrangement is movable along the thrust axis between the position of rest and the triggering position. Each of the couplings comprises a coupling input member and a coupling output member. The triggering arrangement, through its axial displacement along the thrust axis, brings about a relative displacement of these members, whereby these are able to be brought into engagement or out of engagement with respect to each other. in some embodiments, the triggering arrangement is constructed as a push button which is able to be pushed into the housing along the thrust axis. However, it is also conceivable that the triggering arrangement comprises, for example, a sleeve which surrounds the proximal end of the housing at least partially along the peripheral direction.

In some preferred embodiments, each of the couplings is formed by longitudinal grooves and longitudinal ribs on radial inner or outer surfaces of the respective coupling input member or coupling output member. These longitudinal grooves and longitudinal ribs can be brought into and out of engagement in the manner of a tongue-and-groove connection by reciprocal longitudinal displacement of the coupling input members and coupling output members. Such an arrangement is very space-saving compared with other conceivable forms, e.g. teeth, textures or toothings on the end face or oblique toothings, and it makes it possible that, for example, a coupling input member extends both in proximal and also in distal direction beyond the corresponding coupling output member.

In a preferred embodiment, the entire drive arrangement is arranged so as to be displaceable along the thrust axis, so that the movement of the triggering arrangement from the position of rest into the triggering position brings about a distal displacement of the drive arrangement out of its initial position. This makes possible a compact development of an injection device in accordance with the present invention. In some preferred embodiments, the drive arrangement is spring-loaded along the thrust axis in proximal (rearward) direction, to ensure an automatic return of the drive arrangement to its initial position at the end of an administering. Further springs for this purpose can be dispensed with, because the spring-loaded drive arrangement at the same time also pushes the triggering arrangement back to the position of rest.

In some preferred embodiments, an injection device in accordance with the present invention comprises a detachable receptacle holder to hold a reservoir or container containing the product. The delivery element is movable along the thrust axis between a proximal (rear) initial position and a distal (front) final position. A dose limiting element is movable between an initial position and a dose limiting position and cooperates with the dosing arrangement such that it prevents a setting or selecting of a dose, the administering of which would require a movement of the delivery element beyond its distal final position, by it forming a stop in the dose limiting position. As the distal end position of the delivery element generally corresponds to a situation in which the reservoir is emptied except for a residual amount, the dose limiting element therefore prevents a dose from being set on the dosing arrangement which exceeds the available amount of the product. With or during a change of reservoir, the delivery element automatically moves into the distal final position. For this, the device comprises a spring element which produces a spring force which acts on the delivery element along the thrust axis in the distal direction with respect to the housing and brings about a movement of the delivery element into its distal final position, when the receptacle holder is detached from the housing. At the same time, the dose limiting element is automatically brought into its dose limiting position. For this, the dose limiting element, at least in a state in which the receptacle holder is detached from the housing, is coupled with the delivery element such that the movement of the delivery element into its distal final position brings about a movement of the dose limiting element into its dose limiting position. After the receptacle holder has been detached from the housing, the delivery element is therefore in its distal final position and the dose limiting element is in its dose limiting position. When, in this state, the delivery element is moved in the direction of its proximal final position, the dose limiting element continues to remain coupled with the delivery element, so that this movement of the delivery element brings about a proportional movement of the dose limiting element in the direction of its initial position.

Upon or during insertion of a new reservoir, the stopper of the reservoir will push the delivery element into the housing, and namely by an amount which corresponds precisely to the available amount of product in the reservoir. Through the coupling with the dose limiting element, this is also moved by a corresponding amount, so that after the insertion of the reservoir the dose limiting element will lie away from its dose limiting position by an amount which corresponds precisely to the available amount of product. In this way, it is ensured on the one hand that a correct administering takes place at any time, even when the reservoir, on insertion, was only partially filled, and that the dose limiting arrangement also functions correctly in this case. In some preferred embodiments, to make this possible the couplings, in a state in which the receptacle holder is detached from the housing, are uncoupled.

In some preferred embodiments, the delivery element is in a thread or threaded engagement with the input member of the delivery arrangement such that a movement of the delivery element into its distal final position leads to a rotary movement of the input member. The dose limiting element is then coupled with the input member such that the rotary movement of the input member brings about a movement of the dose limiting element into its dose limiting position.

In some embodiments, the delivery element can have an internal thread, the thread axis of which runs along the thrust axis. The input member then comprises an external thread which is in engagement with the internal thread. Thereby, the outer side of the input member can be developed so that it can be easily sealed with respect to the housing, e.g. so that it has a substantially smooth region. In addition, the appearance of the injection device can thus be improved for a user.

In some preferred embodiments, the dose limiting element can be constructed in a sleeve-shape (cylindrical) or a ring-shape (annular). It is arranged locked against rotation and displaceable along the thrust axis relative to the input member and is in engagement via a thread with a further element such that a rotation of the dose limiting element leads at the same time to a displacement of the dose limiting element along the thrust axis, as long as the further element is stationary with respect to the housing. In some preferred embodiments, the further element is a part of the drive arrangement which carries out the drive rotary movement during the administering. By the first coupling being coupled during the administering, no movement of the dose limiting element along the thrust axis takes place during the administering, because both the input member of the delivery arrangement and also the drive arrangement rotate at the same angular speed, whereas, however, in the state in which the receptacle holder is detached from the housing and in which therefore the first coupling is released, a thrust of the delivery element also leads to a displacement of the dose limiting element.

In one preferred development, the injection device comprises a carrier element rotatably arranged relative to the housing. The carrier element is guided with respect to the housing such that on fastening of the receptacle holder on the housing (or connecting it thereto) and on detaching the receptacle holder from the housing (or disconnecting it), it is entrained by the receptacle holder and is set into a movement which comprises a rotary movement about the rotation axis. In the holding position of the receptacle holder, a detent element, e.g. spring-loaded axially by a spring element, then brings about a detachable detent connection, by which the carrier element is fixed relative to the housing. This, in turn, then holds the receptacle holder. The receptacle holder is therefore fixed indirectly, via the carrier element, relative to the housing. Thereby, a great freedom is made possible in the design of the receptacle holder and of the detent element and spring element.

In one embodiment, the device comprises a guide element arranged so as to be locked against relative rotation with respect to the housing, which guide element can be constructed as a guide sleeve. This guide element can be rigidly connected with the housing, can be produced integrally therewith, or it can be displaceable axially with respect to the housing. The carrier element, which can likewise be formed as a sleeve and can then be designated as a bayonet sleeve, is then connected rotatably with the guide element. The spring element and the detent element are arranged so as to be locked against relative rotation with respect to the guide element, and in the holding position of the receptacle holder the detent element is engaged detachably with the carrier element. The guide element can be connected so as to be axially displaceable with respect to the housing and the carrier element can be connected rotatably, but axially secure as regards displacement, with the guide element. Through this configuration, it is made possible that further parts of the device, arranged in the housing, which are connected with the guide element, are displaced axially, when the receptacle holder is detached from the housing. Thereby, it can be achieved that the couplings which are described above are uncoupled.

in some preferred embodiments, the carrier element is guided with respect to the housing such that on fastening of the receptacle holder to the housing it is entrained by the receptacle holder and is set into a combined rotational movement about the rotation axis and translation movement along the rotation axis in a proximal direction.

in some preferred embodiments, the carrier element is moveable between two defined final positions, and the detent element brings about in both positions a detachable detent connection, by which the carrier element is fixed relative to the housing. The carrier element assumes its first final position when the receptacle holder assumes its holding position, and it assumes its second final position when the receptacle holder is removed from the housing. In some preferred embodiments, the detent element is detachably engaged both in the first final position and also in the second final position directly with the carrier element.

in some preferred embodiments, the carrier element is guided in at least one guide slit relative to the housing, i.e. on the actual housing itself or on an element which is fixed to the housing, e.g. by one or more corresponding pins. Likewise, on fastening to the housing, the receptacle holder is guided in at least one guide slit, in the manner of a bayonet connection, relative to the housing.

In some preferred embodiments, the detent element is constructed in the form of a ring which extends around the rotation axis and around the thrust element. Suitable detent noses can be constructed on the ring. This detent element can be axially spring-loaded by a separate spring element. This may be, for example, a helical spring which is subjected to pressure, or another type of elastic element. However, the spring element has the form of a ring which extends around the rotation axis and is curved about an axis perpendicularly to the rotation axis, so that the spring, force is produced by a compressing of the spring element along the rotation axis.

In some preferred embodiments, the detent element is constructed integrally with the spring element. This leads to a simple development. Tthe detent element can be constructed as a projection, protruding in the direction of the rotation axis, on the spring element. This is advantageous when the spring element, as described above, has the form of a curved ring.

In some embodiments, the injection device can further have at least one ball bearing which absorbs forces which are transmitted between the delivery element and the housing. By a ball bearing being provided, frictional losses caused during the administering owing to the transmission of forces between the delivery element and the housing, are largely minimized.

In some preferred embodiments, the ball bearing is advantageously arranged such that it absorbs (axial) forces acting along the thrust axis, which are transmitted from the delivery element (locked with respect to rotation relative to the housing) via the rotatable element to the housing, i.e. which act between the rotatable element and the housing. Expressed in general terms, axial forces, e.g. acting in proximal direction, are therefore transmitted between the delivery element and the housing via a rotatable connection which is secure with respect to displacement in axial direction. For this, in the prior art, generally a sliding connection is provided between the rotatable element and the housing or an element which is fixed to the housing. In the present embodiment, on the other hand, at least one ball bearing is provided, which is arranged between the rotatable element or an element connected therewith on the one hand, and the housing or an element which is fixed to the housing at least during the administering, on the other hand. Thereby, frictional losses during the rotation of the rotatable element can be avoided.

In some preferred embodiments, two ball bearings are present, which are arranged so that they can absorb forces along the thrust axis both in a proximal (rearward) direction and also in the opposite, distal (forward) direction, i.e. the direction in which the thrust takes place. Axial forces in the proximal direction occur generally during the administering, whereas axial forces in the distal direction can occur when the delivery element is spring-loaded in the distal direction, as may be the case in some preferred embodiments. The spring serving for this is sufficiently weak that it does not cause any ejection of the product out of the reservoir. Rather, it serves, in a change of reservoir, to automatically bring the delivery element into its distal final position, i.e. to extend it completely, when the reservoir is removed from the housing. When the delivery element is in a suitable connection with the rotatable element, this leads to the rotatable element being set into a rotation when the delivery element moves out due to the spring force. To keep the spring force, which is necessary for this, small, a ball bearing is advantageous, because with the extending of the delivery element, it minimizes the frictional forces acting then.

BRIEF DESCRIPTION OF THE DRAWINGS

FIG. 6 is a perspective view of a coupling sleeve;

FIG. 11A is a longitudinal section through selected parts of the injection device of FIG. 1A with a dose limiting ring in its final position;

FIG. 11B is a longitudinal section through selected parts of the injection device of FIG. 1A with the dose limiting ring in its initial position;

FIG. 12A is a perspective view of a coupling shaft with a dose limiting ring of the injection device of FIG. 1A;

FIG. 12B is the parts of FIG. 12A in an exploded view;

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc. Generally, unless otherwise indicated, relative positional or orientational terms (e.g., upwardly, downwardly, above, below, etc.) are intended to be descriptive, not limiting.

Figures 1A, 1B:
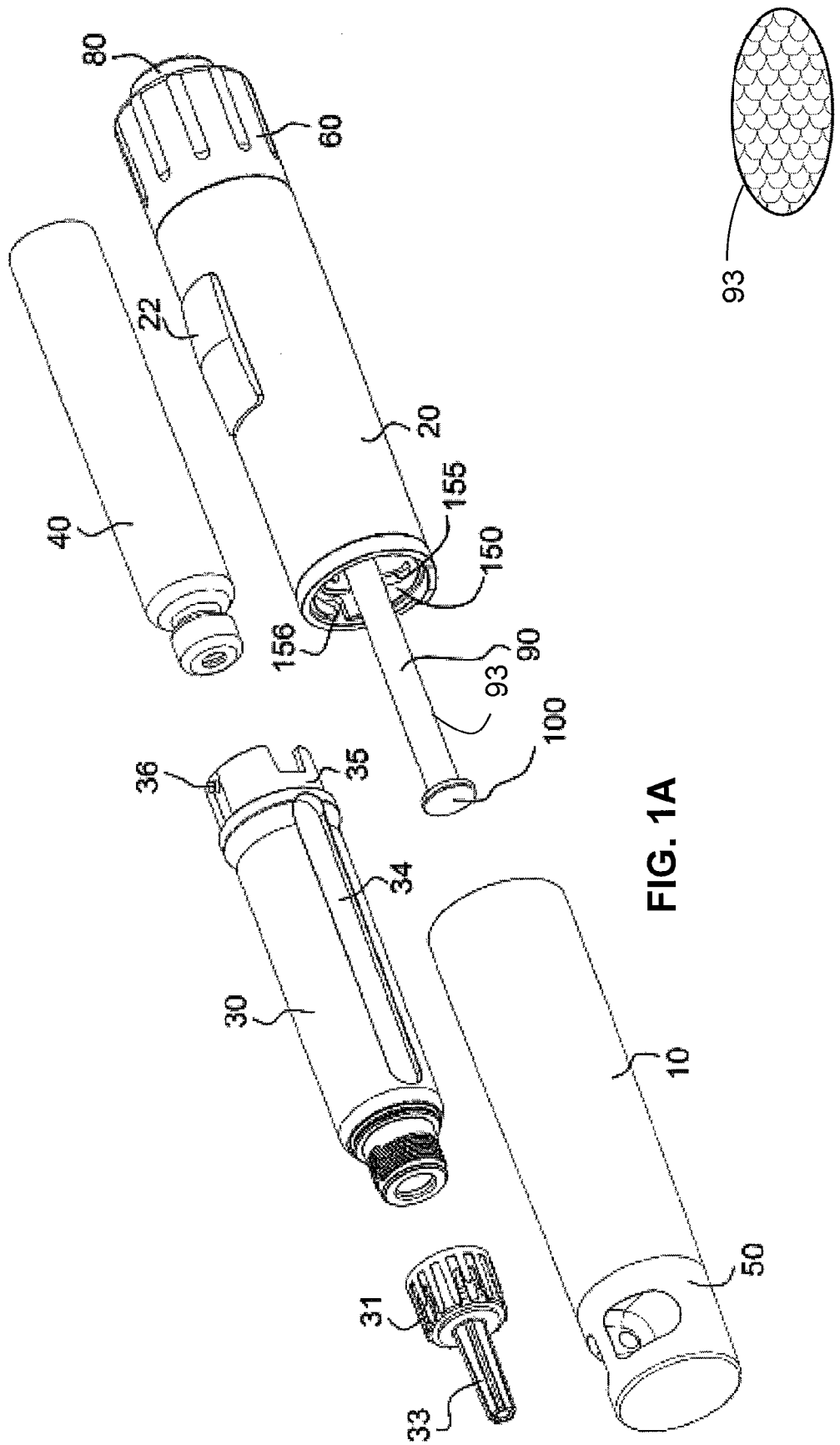
FIG. 1A is a perspective exploded view of an exemplary embodiment of an injection device according to the present invention.
FIG. 1B is a detail view of a surface structure provided on the thrust sleeve.
Figure 2:
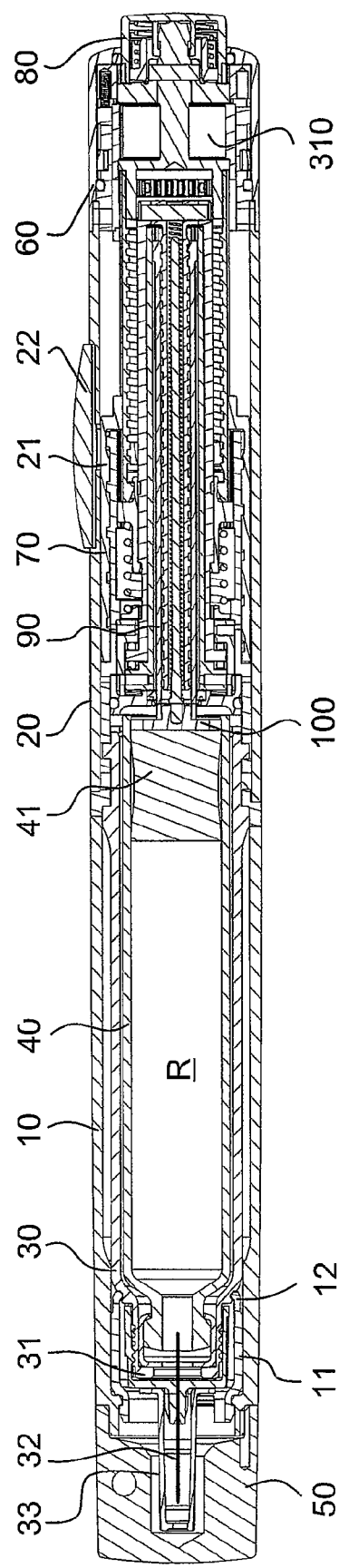
FIG. 2 is a longitudinal section through the injection device of FIG. 1A.

FIG. 1A depicts an injection device in the form of an injection pen in a perspective exploded view. FIG. 2 shows the device in longitudinal section. The following description relates to the device in the assembled state, as is illustrated in FIG. 2.

The injection device has a housing sleeve 20 in which a mechanism is housed for setting and distributing a dose. The housing sleeve 20 has substantially the form of a circular cylinder and defines a longitudinal axis. A receptacle holder in the form of a carpule sleeve 30 is detachably fastened to a distal end of the housing sleeve 20 by a bayonet connection, which is described in further detail below. This receives a receptacle in the form of a carpule 40 with a fluid medicament, in which a stopper 41 is displaceably guided. A medicament reservoir R of changeable volume is thereby delimited inside the carpule. Instead of a carpule, a different receptacle can also be present, the volume of which is changeable, e.g., a receptacle with walls folded in a concertina-like manner in the manner of a bellows. The content of the carpule 40 may be monitored through an elongated viewing window 34 in the carpule sleeve 30. A needle holder 31 is screwed on the distal end of the carpule sleeve 30, which needle holder 31 carries a hollow needle (cannula) 32, serving as injection needle, the proximal end of which projects through a sealing septum into the medicament reservoir R. A removable needle protection sleeve 33 surrounds the forwardly projecting region of the needle 32 and protects a user from being pricked accidentally. A protective sleeve 10, the distal end of which is permanently closed by a protective cap 50, is pushed over the carpule sleeve 30. A holding ring 11 with detent arms 12 extending in the proximal direction is mounted inside the protective sleeve 10. The ends of the detent arms 12 are detachably engaged with the carpule sleeve 30. The proposed embodiments are described here by an injection device which has a needle 32, but it is also conceivable that the injection device has several needles or no needle, as in a jet injector.

At the proximal end of the housing sleeve 20, a dosing sleeve 60 is rotatably arranged with a push button 80 held therein. The dosing sleeve serves for the setting of a dose, which is to be distributed from the medicament reservoir R, and for the tensioning of a drive arrangement with a drive element in the form of a spiral spring 310, acting as a torsion spring. The set dose is displayed on a display drum 70, and can be read through a window 21 in the housing sleeve 20, which is covered by a transparent covering 22. A correcting (reduction) of the set dose may be possible by turning back the dosing sleeve 60, which is described in further detail below.

With reference to these parts, the following directions can be defined, which will be referred to consistently below: The distal (forward) direction is the direction in which the administering takes place, i.e., it points along the longitudinal axis from the push button 80 in the direction of the hollow needle 32. The proximal (rearward) direction is accordingly defined as the opposite direction. If reference is made to a direction of rotation (clockwise, anticlockwise), this means the direction of rotation which one observes when one views along the longitudinal axis in the distal direction.

After the setting of the dose, the hollow needle 32 is pierced through the skin of the patient, and a distribution of the dose is triggered by the user pushing the push button 80 into the dosing sleeve 60. A rotary movement is produced by the drive arrangement via a mechanism, which is described in detail below, this rotary movement being converted into an advancing of a delivery element in the form of a thrust sleeve 90 in the distal direction. The thrust sleeve 90 pushes the stopper 41 of the medicament carpule 40 by the set amount in the distal direction via a thrust flange 100 arranged at its distal end, whereby the distribution of the medicament is brought about out of the reservoir R. The thrust sleeve 90 therefore acts as a piston rod for the piston which is formed by the thrust flange 100 and the stopper 41. After the end of the administering, the user releases the push button 80 again. During the advance of the thrust sleeve 90, the display drum is entrained by the drive arrangement such that it returns to its zero position in the course of the distribution. The injection pen is thereby immediately ready for the next dose setting.

When the medicament or therapeutic substance in the medicament reservoir R is running low, i.e. the thrust sleeve 90 is almost completely extended, this is detected by a dose limiting arrangement in the injection pen, which is described in further detail below. The dose limiting arrangement allows the user to set as a maximum the remaining available residual dose. In a subsequent carpule or ampuole change, the dose limiting arrangement and also the display drum 70 automatically return into the initial state, and manual resetting may be unnecessary.

The structure and mode of operation of the mechanism are described in detail below.

Figure 3:
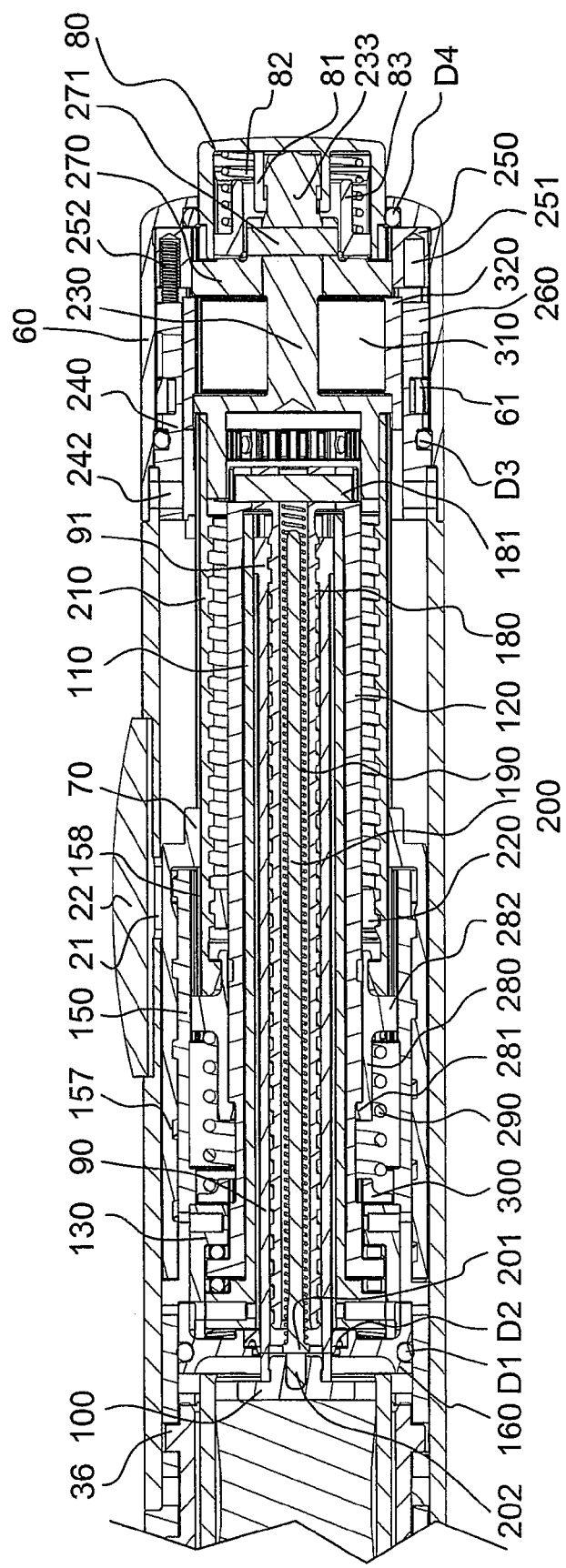
FIG. 3 is an enlarged cut-out of FIG. 2.

FIG. 3 shows an enlarged illustration of the rear (proximal) region of the injection device of FIG. 1A. The structure of this region will now be described in detail substantially from the interior outwardly.

The thrust sleeve 90 is mounted in a guide sleeve 110, arranged such that it is locked against relative rotation with respect to the housing and displaceably, locked against relative rotation and displaceably in the longitudinal direction. For this, the thrust sleeve 90 has, at its proximal end, several radially outwardly projecting guide cams 91, which are guided in longitudinal grooves, complementary thereto, on the inner side of the guide sleeve 110.

Figure 4:
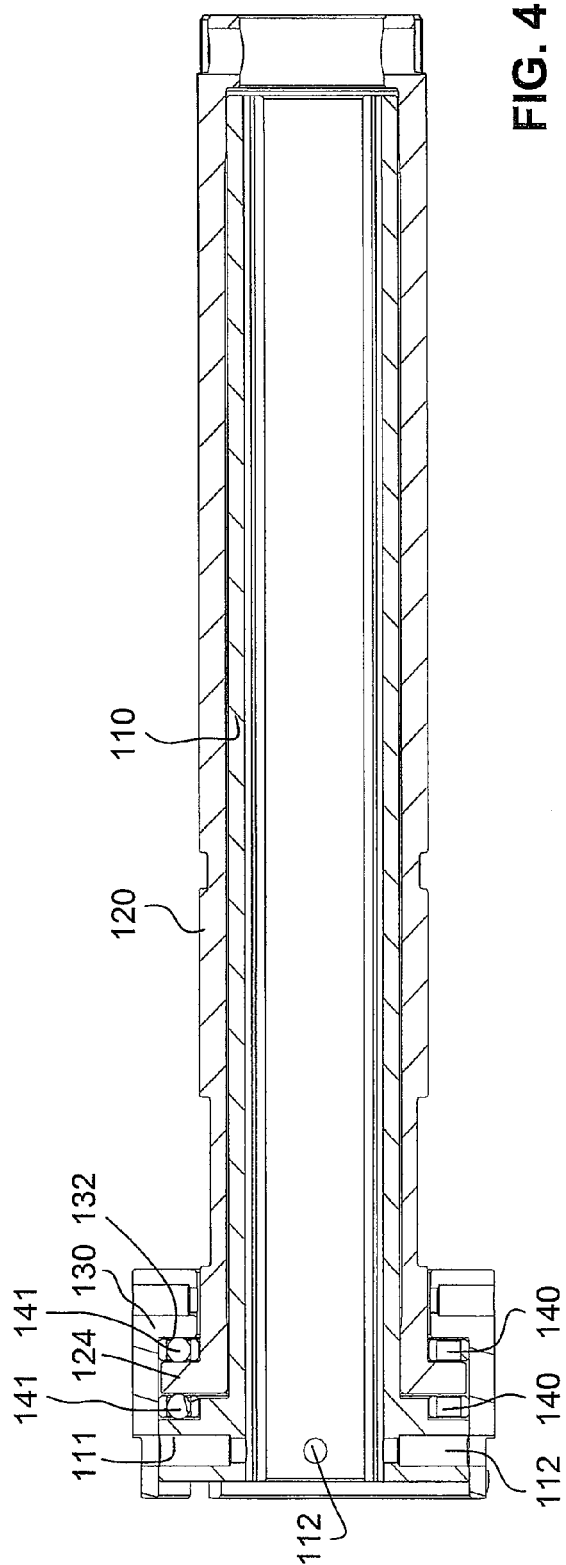
FIG. 4 is a longitudinal section through an arrangement of a guide sleeve and of a coupling sleeve in the injection device of FIG. 1A.

The guide sleeve 110 can be seen in FIG. 4, which illustrates the cooperation of the guide sleeve 110 with further parts. The guide sleeve 110 has at its distal end a radially outwardly projecting, circumferential ring flange 111 with radial bores 112. A ring-shaped bearing holder 130 is pushed from the proximal side via the guide sleeve 110, surrounds the ring flange 111 radially and is connected rigidly therewith via radial cylinder pins, which are not illustrated in the drawings.

A coupling sleeve 120 is rotatably mounted between the ring flange 111 of the guide sleeve 110 and an inwardly projecting shoulder 132 of the bearing holder 130. As is described in further detail below, the coupling sleeve 120 is connected via a threaded rod 180 with the thrust sleeve 90 and therefore forms a part of a delivery arrangement, which is driven by a rotary movement and brings about a thrust of the delivery element in the form of the thrust sleeve. The coupling sleeve 120 therefore absorbs considerable axial forces in operation, which are transmitted via its bearing onto the guide sleeve 110, the bearing holder 130, the mechanism holder 150 and therefore to the housing.

To construct the bearing so as to be low-loss, the bearing includes ball bearings for providing relatively low friction to a rotating unit. Accordingly, a first ball bearing ring 140 is provided between the flange 111 of the guide sleeve and a radially encircling flange 124 of the coupling sleeve 120. A further such ball bearing ring 140 is arranged between the flange 124 and an end face of the bearing holder 130.

Figure 5B:
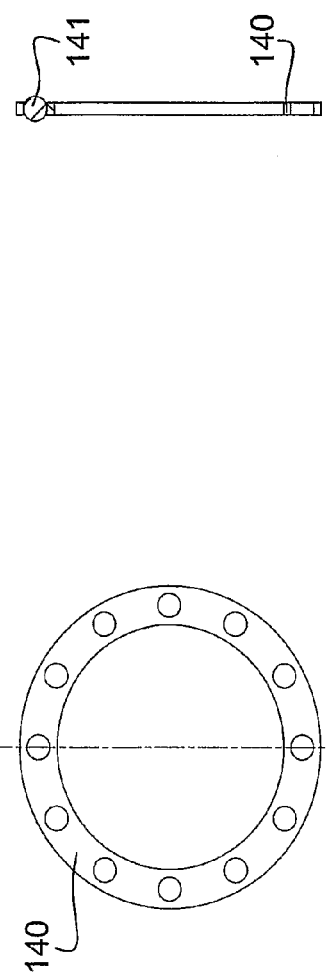
FIG. 5B is a sectional view of the ball bearing ring in the plane A-A.
Figure 5A:
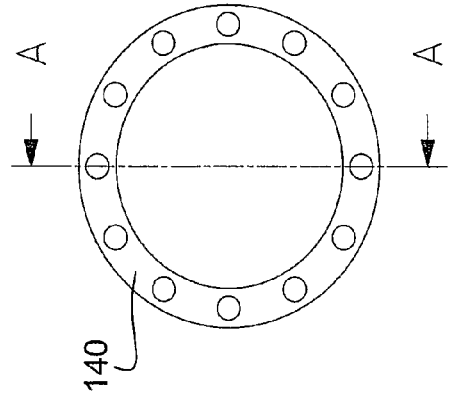
FIG. 5A is a top view onto a ball bearing ring.

The ball bearing ring 140 is illustrated in detail in FIGS. 5A and 5B. It carries a plurality of bearing balls 141, i.e., twelve, but may include a range of bearing balls such as from 3 to 24. The bearing balls 141 run or roll, as can be seen in FIG. 3, in flat, circular grooves formed in both end faces of the radial flange 124 of the coupling sleeve 120, in the corresponding end face of the flange 111 of the guide sleeve 110 and in the end face of the bearing holder 130.

The coupling sleeve 120 is illustrated in FIG. 6, together with the ball bearing rings 140 (but without balls 141). On the cylindrical sleeve body 121, a plurality of longitudinal ribs 122 are formed, which extend over a considerable part of the length of the sleeve body in a longitudinal direction up to its proximal end. Corresponding grooves are provided therebetween. From a thickening area 123, the flange 124 follows towards the front, which adjoins the ball bearing rings 140 on both sides.

Figure 7:
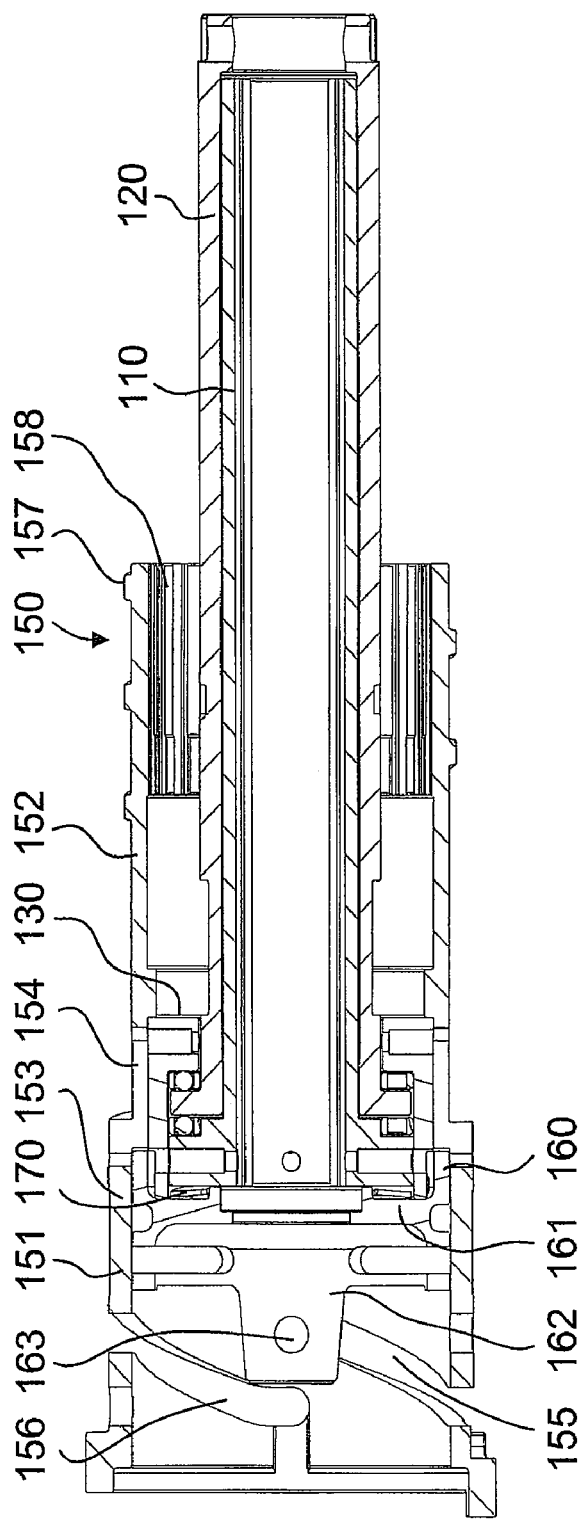
FIG. 7 is a longitudinal section through selected parts of the injection device of FIG. 1A.

FIG. 7 illustrates how the unit of guide sleeve 110 and bearing holder 130 is held in a sleeve-shaped mechanism holder 150, so as to be locked against relative rotation, but displaceably arranged in the longitudinal direction.

The mechanism holder 150 includes a distal section 151 with increased internal and external diameter and a proximal section 152 with a somewhat smaller internal and external diameter. These two sections are connected by a step 153. The outer side of the distal section 151 is held rigidly in the housing sleeve 20. Thereby, the mechanism holder 150 may be immovable with respect to the housing, therefore forming functionally a part of the housing.

Adjoining the step 153, at least two longitudinal slits 154 are formed in the mechanism holder 150. Pins, which are not illustrated in FIG. 7, are inserted in the bearing holder 130. These project radially beyond the bearing holder 130 and into the longitudinal slits 154 of the mechanism holder. The bearing holder 130 and the guide sleeve 110, which is securely connected therewith, may thus be guided displaceably between a distal and a proximal final position and so as to be secured with regard to rotation in the mechanism holder 150. Toward the proximal end, on the outer covering surface of the mechanism holder 150, an external thread 157 is formed. Several longitudinal grooves 158 are formed in this region on the inner surface.

Figure 8:
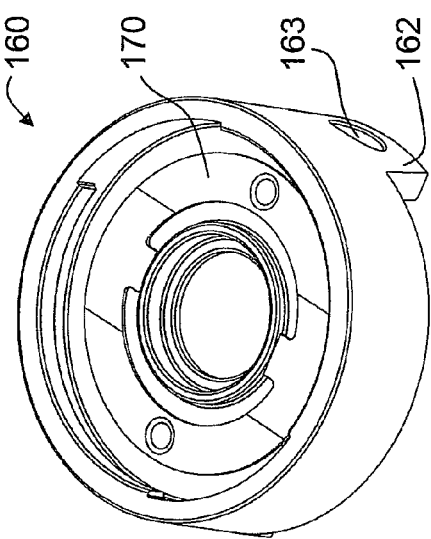
FIG. 8 is a perspective illustration of a bayonet sleeve.

In the distal direction, a bayonet sleeve 160 adjoins the guide sleeve 110 and the bearing holder 130, which is also illustrated in FIG. 8. It is held on the bearing holder 130 in the axial direction and is rotatable with respect thereto. With an inwardly projecting ring flange 161, the bayonet sleeve 160 supports the unit of guide sleeve 110 and bearing holder 130, with coupling sleeve 120 held therein, in the distal direction. The bayonet sleeve 160 has two arms 162 projecting axially in the distal direction and lying diametrically opposite each other, which arms 162 have radial openings 163. Radially outwardly projecting pins are inserted into these openings, which pins run in two guide slits 155 of the mechanism holder 150 acting as connecting link guides (positive guides). Guide slits 155 are configured so that the bayonet sleeve 160, with an anticlockwise rotation (in the sense of the definition indicated above, i.e., on observation along the longitudinal axis in the distal direction) is compulsorily also moved axially in the proximal direction. In this way, the unit of guide sleeve 110, bearing holder 130 and coupling sleeve 120 is moved in the proximal direction. Vice versa, with a rotation of the bayonet sleeve 160 clockwise, this unit moves in the distal direction. Parallel to the guide slits 155, a further pair of guide slits 156 runs, in order to receive radial pins 36 of a locking region 35 of the carpule sleeve 30 (cf. FIGS. 1 and 3). On introduction of the carpule sleeve 30 into the housing, the carpule sleeve is also subject to a positive guidance, so that the carpule sleeve 30 performs a combined rotary movement and displacement. The carpule sleeve 30 is configured such that, upon its movement, it is coupled with the arms 162 of the bayonet sleeve 160 and entrains the bayonet sleeve 160.

The guide slits 155 are of finite length and delimit the movement of the bayonet sleeve between a distal and a proximal final position. In FIG. 7, the proximal final position is illustrated in which the guide slits 155 allow a rotation of the bayonet sleeve through 90 degrees between these positions.

Figure 9A:
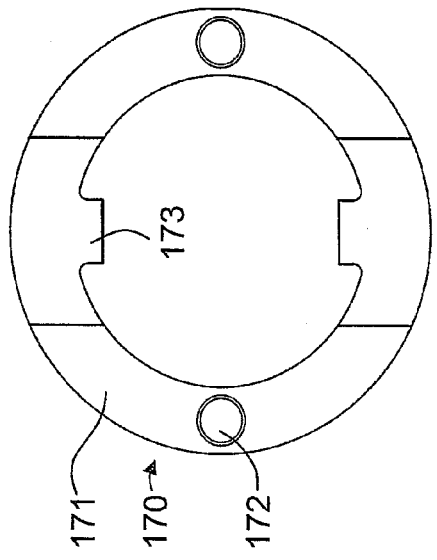
FIG. 9A is a top view onto a bayonet spring.
Figure 9C:
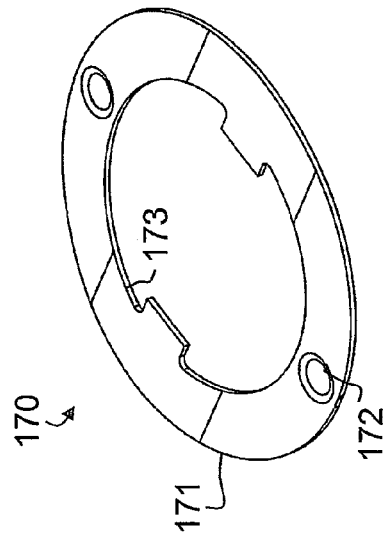
FIG. 9C is a perspective view of the bayonet spring of FIG. 9A.
Figure 9B:
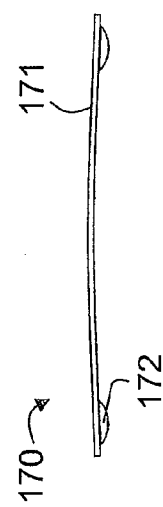
FIG. 9B is a side view of the bayonet spring of FIG. 9A.

To fix the bayonet sleeve detachably in its two final positions so as to be locked against relative rotation with respect to the guide sleeve 110, and thus with respect to the housing sleeve 20, a bayonet spring 170 is arranged between the bayonet sleeve 160 and the guide sleeve 110. This is illustrated, in detail, in FIGS. 9A to 9C. The bayonet spring 170 has a substantially flat and ring-shaped base body 171 acting as a spring element. Two diametrically opposite, axially flatly projecting bulges or projections 172 protrude out from this base body as detent elements or detent cams axially in the distal direction. Two diametrically opposite flat tongues 173 protrude inwardly and come to lie in corresponding flat recesses of the guide sleeve 110. Thereby, the bayonet spring 170 is held, so as to be secured with regard to torsion, on the guide sleeve 110. As can be seen from FIG. 9B, the base body 171 is bent slightly about an axis perpendicular to the longitudinal axis, and namely such that the curvature mid-point lies on the same side of the bayonet spring as the projections 172 (i.e., distal). As a result, the bayonet spring 170 is prestressed between the guide sleeve 110 and the bayonet sleeve 160 permanently such that the projections 172 are pressed in the distal direction against the corresponding counter-surface on the ring flange 161. In this counter-surface, four depressions are present, which are arranged at intervals of 90 degrees about the longitudinal axis. In the proximal final position, the projections 172 come to lie in a first pair of these depressions, whereas in the distal final position, in which the bayonet sleeve is turned through 90 degrees, they are held in the second pair of the depressions. Thereby, two defined detent positions are provided, in which the bayonet sleeve 160 engages via the bayonet spring 170 with the projections 172 detachably with the guide sleeve 110. In both positions, a certain force may need to be overcome to move the bayonet sleeve in the direction of the respective other final position again. Each of the depression pairs may comprise a different configuration, e.g., depth and/or shape, so that a different releasing force is necessary in the two detent positions.

In one detent position, the carpule sleeve 30 is held via its coupling with the bayonet sleeve 160 to be secure with regard to rotation and displacement on the guide sleeve 110, and thus on the housing. In the other detent position, the carpule sleeve 30 is detached from the housing. In this position, the bayonet sleeve 160 is again engaged with the guide sleeve 110 and is thereby fixed on the housing 20 so as to be secure with regard to rotation and displacement. In this way, the carpule sleeve, on insertion into the guide slits 156, locates the arms 162 of the bayonet sleeve in the correct position around the longitudinal axis, and can entrain these upon the releasing of the detent connection.

In the present example, the detent elements are constructed as projections 172 integrally formed with the spring element in the form of the base body 171. Alternatively, a separate detent element may be provided, e.g., in the form of a rigid ring with detent cams, which may be pressed in the axial direction by the spring element. As an alternate to projections, the detent element may also have depressions, which then cooperate with corresponding projections of the counter surface. In the present example, the detent element is locked against relative rotation with respect to the housing. Alternatively, it can also be locked against relative rotation with respect to the bayonet sleeve. The spring element may also have an alternative configuration to produce an axial force. Accordingly, various modifications of locking between the carpule sleeve 30 and the housing are contemplated.

Figure 10:
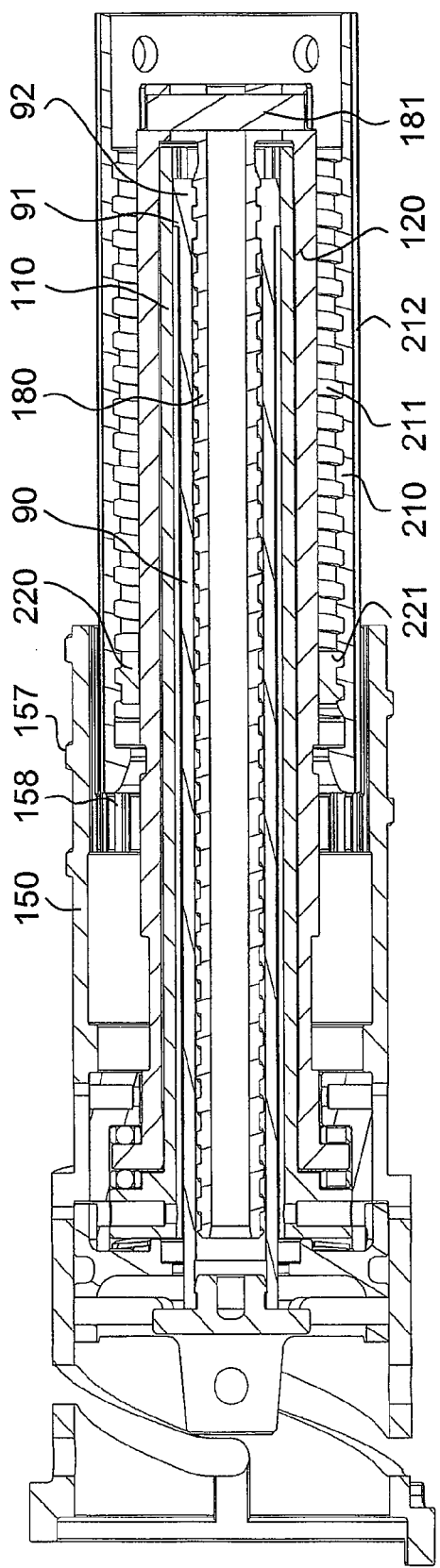
FIG. 10 is a longitudinal section through selected parts of the injection device of FIG. 1A.

In FIG. 10, the parts of the injection device illustrated in FIG. 7 are illustrated together with the thrust sleeve 90 arranged in the guide sleeve 110. At its proximal end, the thrust sleeve 90 has a short internal thread 92 in which a hollow external threaded rod 180 is guided. The latter is connected at its proximal end rigidly with the coupling sleeve 120 via a transverse pin 181. A thrust of the thrust sleeve 90 in the distal direction takes place, by the coupling sleeve 120, which is rotatably mounted, carrying out a rotary movement. As a result of the rigid connection between coupling sleeve 120 and external threaded rod 180, this rotary movement also brings about a rotation of the external threaded rod 180. The thrust sleeve 90 runs with its internal thread 92 on the external threaded rod 180, similar to a nut. The thrust sleeve 90 is locked against relative rotation with respect to the guide sleeve 110, because it runs via the guide cams 91 in longitudinal grooves on the inner side of the guide sleeve 110. In this way, the thrust sleeve 90 is advanced axially on a rotation of the external threaded rod 180. Accordingly, a rotary movement of the coupling sleeve 120 is converted into an axial displacement of the thrust sleeve 90.

As can be seen from FIG. 3, the thrust sleeve 90 is assisted in this thrust movement by a long helical spring 190, which is subjected to pressure, and which is arranged in the interior of the threaded rod 180 and is guided on a guide needle 200. The helical spring 190 presses a ring-shaped thickening 201 close to the distal end of the guide needle 200 in the distal direction against the thrust flange 100. An axial pin 202 projects into a corresponding blind-end bore of the thrust flange 100 and is rotatable in this blind-end bore.

Figure 12C:
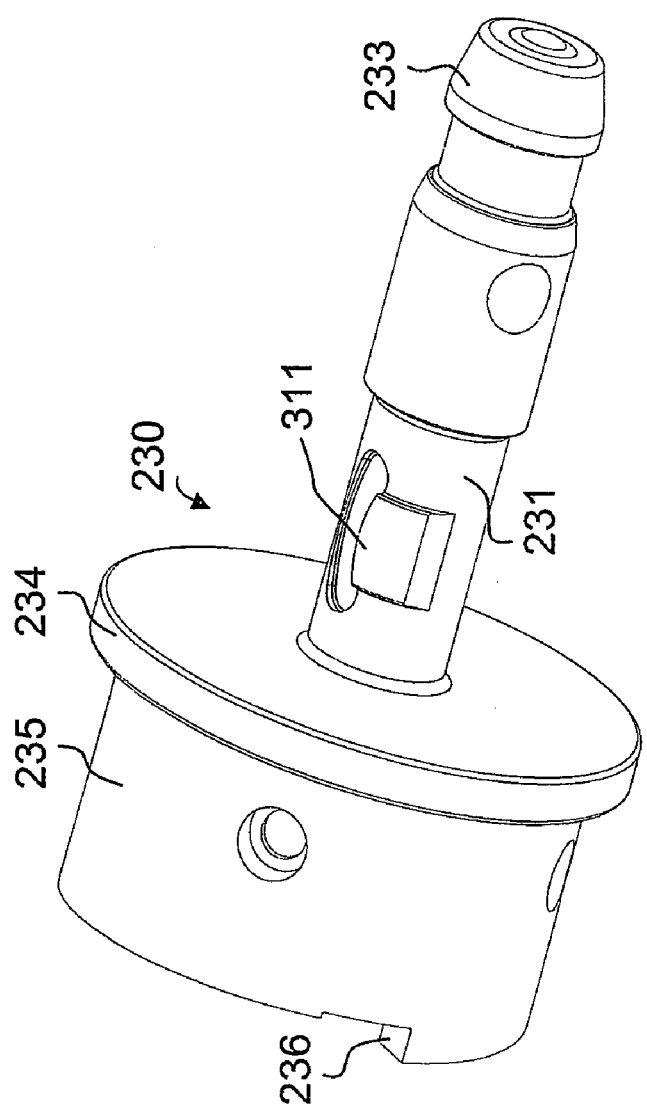
FIG. 12C is the coupling shaft of FIG. 12A in a perspective view from another direction of view.

Furthermore, in FIG. 10 a substantially cylindrical transmission sleeve 210 is inserted into the mechanism holder 150 from the proximal side, which transmission sleeve partially surrounds the coupling sleeve 120. The transmission sleeve 210 has on the outer side a plurality of longitudinal ribs 212. The external diameter of the transmission sleeve 210 is selected here so that, despite its external longitudinal ribs, it is freely rotatable inside the mechanism holder 150. On the inner side, the transmission sleeve 210 has an internal thread 211, in which a dose limiting ring 220 runs with a corresponding external thread 221. In the interior of the dose limiting ring 220, longitudinal grooves 222 are present which can be seen in FIGS. 12A and 12B, into which the longitudinal ribs 122 of the coupling sleeve 120 (cf. FIG. 6) engage. Thereby, the dose limiting ring 220 is movable on the one hand so as to be secure with regard to rotation in the axial direction on the coupling sleeve, and on the other hand is guided in the internal thread of the transmission sleeve 210. A rotation of the coupling sleeve 120 with respect to the transmission sleeve 210 therefore leads to a rotation and axial displacement of the dose limiting ring 220.

The axial displacement range of the dose limiting ring is limited in the distal and proximal directions. This is described in conjunction with FIGS. 11A, 11B, 12A and 12B.

In FIGS. 11A and 11B, a coupling shaft 230 is connected with the transmission sleeve 210. The coupling shaft comprises an axis 231 with a transverse bore 232 close to the proximal end 233. A circumferential flange 234 extends radially outwardly from the distal end of the axis. A ring flange 235 extends in turn therefrom axially in the distal direction. The external diameter of the circumferential flange 234 is greater than that of the ring flange 235, whereby the circumferential flange 234 protrudes radially over the ring flange 235, and forms a stop for the transmission sleeve 210. The ring flange 235 is pushed into the transmission sleeve 210, so that the latter lies with its proximal end against the circumferential flange 234. The ring flange is secured by radial pins in the transmission sleeve 210, which are pushed into bores 237. Thereby, the coupling shaft 230 and the transmission sleeve 210 are connected with each other so as to be locked against relative rotation and secured against displacement. Several longitudinal grooves 238 are formed in the inner surface of the ring flange 235.

FIGS. 12A and 12B show the coupling shaft 230 and the dose limiting ring 220 alone. A radial stop 223, which cooperates with a corresponding radial stop 236 on the ring flange 235 of the coupling shaft, is formed on the dose limiting ring 220. A radial stop is understood to mean a stop surface, the surface normal of which points substantially in the tangential direction, and which is formed to cooperate with a corresponding counter surface. The radial stop is therefore primarily stressed in a tangential direction (i.e., in a rotational direction) instead of in an axial direction. Thereby, a radial stop avoids the risk of jamming, such as when two parts collide axially via a screw connection, e.g., in the case of a small pitch of the helical thread. The radial stop 236 delimits the screw motion of the dose limiting ring 220 in the proximal direction. In FIG. 11A the dose limiting ring 220 is shown in the resulting proximal final position, and in FIG. 11B on the other hand in a distal initial position.

Figure 13:
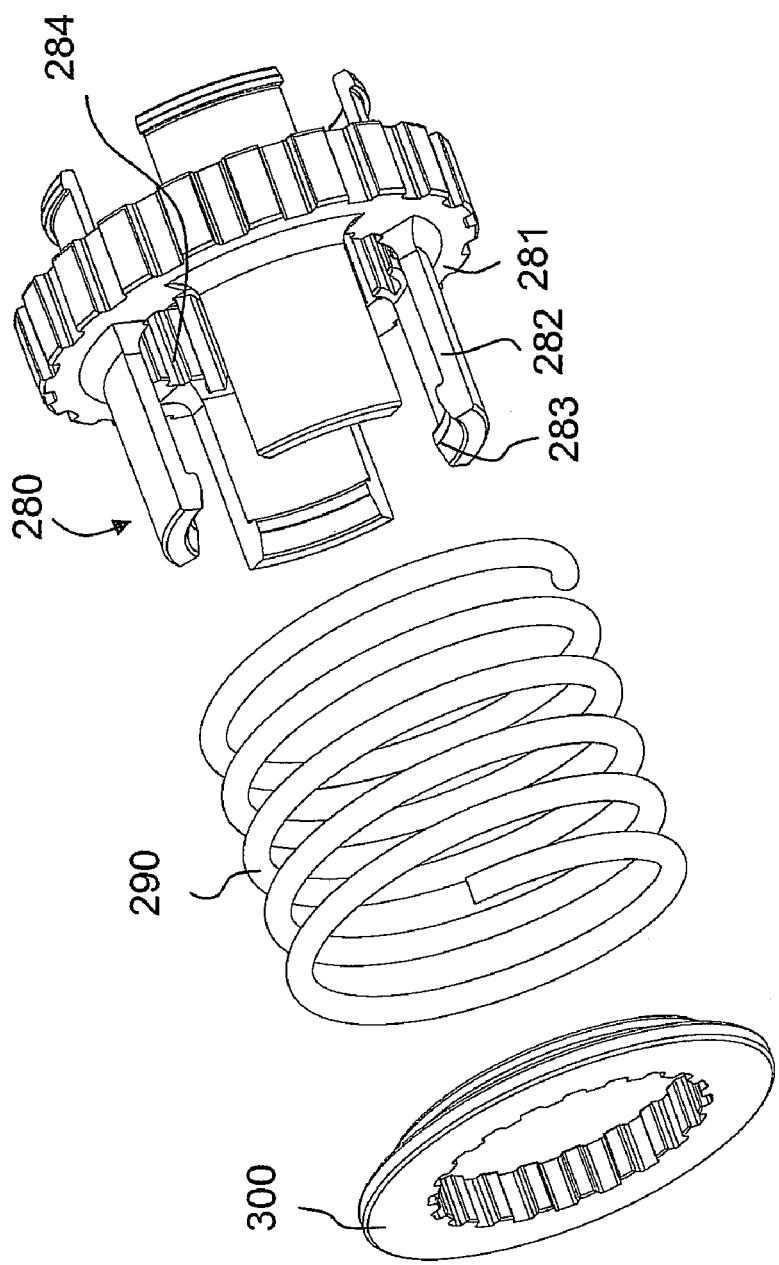
FIG. 13 is an exploded view of an arresting sleeve, a coupling spring and a support ring.

The proximal end of an arresting sleeve 280 is rotatably clicked into an inwardly directed ring flange 213, chamfered in the distal direction, at the distal end of the transmission sleeve 210. For better clarity, the arresting sleeve 280 is not illustrated in FIG. 10. However, it is shown in FIG. 13. The arresting sleeve comprises a ring-shaped main body 281, from which four arms 282 extend in the distal direction. On its inner surface, the main body has longitudinal grooves 284, which are meshed with the longitudinal ribs 122 of the coupling sleeve 120. Thereby, the arresting sleeve 280 is displaceable in the longitudinal direction relative to the coupling sleeve 120, but is secured as regards torsion with respect thereto. At the end of the arms 282, inwardly extending flange regions 283 are present. The possible displacement range is limited in the proximal direction by these flange regions. These abut in the proximal final position of the arresting sleeve 280, as illustrated in FIG. 3, onto the distal end of the longitudinal ribs 122 of the coupling sleeve 120. Longitudinal ribs are formed on the outer peripheral surface of the main body 281. These longitudinal ribs engage, in the position of FIG. 3, into the inner longitudinal grooves 158 of the mechanism holder 150. Thereby, the arresting sleeve 280 is displaceable in this position axially with respect to the mechanism holder 150, but secured with regard to torsion. The arresting sleeve 280 in this position therefore secures the coupling sleeve 120 against a rotation in the mechanism holder 150. As described further below, the arresting sleeve 280 is, however, displaceable so far in the distal direction that it can come out of engagement with the mechanism holder 150 and is then rotatable with the coupling sleeve 120.

The arresting sleeve 280 is pre-stressed in the proximal direction by a coupling spring 290. The coupling spring is configured as a helical spring, which is subjected to pressure, surrounds the arms 282 of the arresting sleeve 280 and lies with its proximal end against the distal end face of the main body 281. At the distal end of the coupling spring 290, the latter is held on a support ring 300, which abuts against the bearing holder 130 in the distal direction and on the inner side of which longitudinal grooves are formed.

Figure 14:
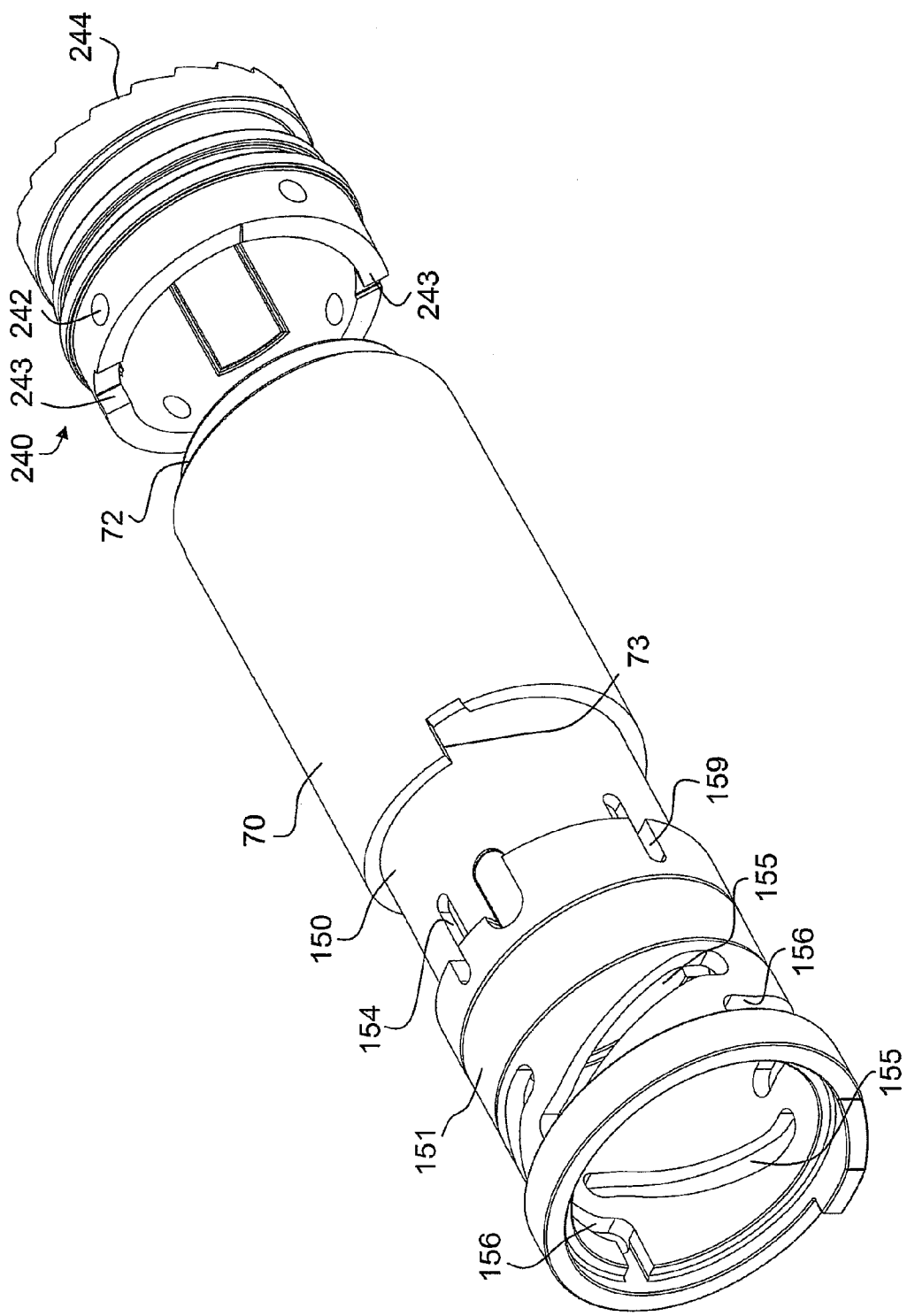
FIG. 14 is a perspective view of selected parts of the injection device of FIG. 1A.

In FIG. 14, the unit of FIG. 10 is illustrated with further components. The display drum 70 is held on the mechanism holder 150. In addition, a stop sleeve 240 is connected immovably with the housing sleeve 20 by pins projecting into the radial holes 242, e.g., see FIG. 14. At the distal end of stop sleeve 240, radial stops 243 are provided, and at the proximal end, teeth 244, e.g., serrated teeth, are arranged on the end face for a ratchet connection, described below.

The display drum 70 has an internal thread, which can be seen in FIG. 3, and runs on the external thread 157 of the mechanism holder, which can be seen in FIGS. 7 and 10. At its proximal end, the display drum 70 narrows to a ring-shaped region 72. Longitudinal grooves are formed on the inner side of the ring-shaped region 72. By these longitudinal grooves, the display drum 70 is secured with regard to torsion, but is guided displaceably in the longitudinal direction on the longitudinal ribs 212 of the transmission sleeve 210. Through the combination of this longitudinal guide on the transmission sleeve and the thread guide on the mechanism holder, a rotation of the transmission sleeve 210 leads to a combined rotation and longitudinal displacement of the display drum 70. This movement is delimited or stopped by radial stops in both directions. At the proximal end, a radial stop cooperates with the radial stop 243 of the stop sleeve 240. At the distal end, a corresponding radial stop 73 cooperates with a radial stop 159 of the mechanism holder 150. Thereby, the screw motion of the display drum 70 is limited in both directions by radial stops.

Figure 15:
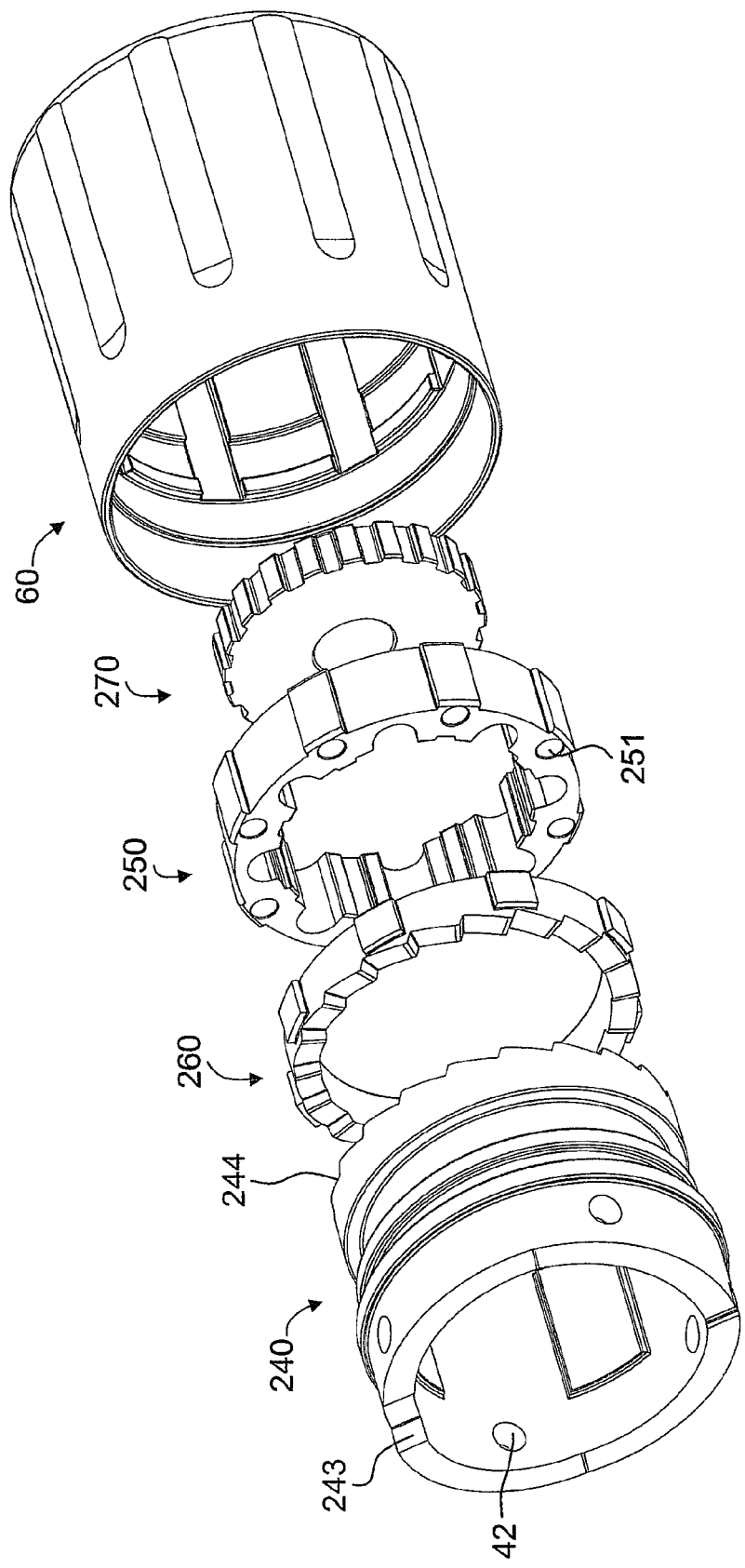
FIG. 15 is a perspective exploded view of the proximal end of the injection device of FIG. 1A.

The mechanism for setting a dose and for triggering its administering is described with reference to FIGS. 3 and 15. The dosing sleeve 60 is arranged at the proximal end of the housing sleeve 20. Dosing sleeve 60 is secured with regard to displacement axially with a spring ring 61 and is fixed rotatably on the stop sleeve 240. The dosing sleeve 60 is rotatable via a slip coupling in the form of a ratchet connection both clockwise and also anticlockwise about the longitudinal axis towards the housing sleeve 20, and is thus configured and arranged to assume several predefined detent positions.

The dose setting mechanism comprises an inner ring 250 arranged inside the dosing sleeve 60 and rigidly connected with the dosing sleeve 60. The inner ring 250 has in its radial inner surface a plurality of longitudinal grooves. In the distal direction from the inner ring 250, a ratchet ring 260 is held axially displaceably but secured with regard to rotation in the dosing sleeve 60. The ratchet ring 260 is serrated on its distal end face, and namely in a complementary manner to the teeth 244 of the serrated proximal end face of the stop sleeve 240, so that teeth of the ratchet ring 260 can engage in depressions on the end face of the stop sleeve 240 and vice versa. The ratchet ring 260 is axially displaceable by a certain amount between the distal end face of the inner ring 250 and the serrated proximal end face of the stop sleeve 240. The amount by which an axial displacement is such that the serrated end faces of the ratchet ring 260 and of the stop sleeve 240 can come out of engagement. The ratchet ring 260 is pressed elastically by an elastic force against the stop sleeve 240. For this, several axial bores 251 are present in the form of blind-end bores in the inner ring 250. Helical springs 252, which are subjected to pressure are inserted in at least one of these bores, e.g., in at least two bores, at a uniform spacing along the circumference of the ring when multiple bores are provided. The helical springs 252 press the ratchet ring elastically against the stop sleeve.

In the position of rest, the ratchet ring 260, with its serrated end face, is in engagement with the serrated end face of the stop sleeve 240. Thereby, the ratchet ring and the dosing sleeve 60 connected therewith assume one of several defined angle positions about the longitudinal axis. With a rotation of the dosing sleeve 60 relative to the housing sleeve 20, the teeth of the ratchet ring 260 and of the stop sleeve 240 slide on each other against the axial spring force of the helical springs 252, until they come out of engagement and arrive in engagement again in the next defined angle position. In this way, an elastically detachable detent connection is produced by rotation with a sufficient torque in several predefined angle positions of the dosing sleeve 60 relative to the housing sleeve 20. This mechanism can also be designated as a double slip coupling.

By rotation of the dosing sleeve 60 clockwise, the spiral spring 310 can be tensioned, which is indicated in FIG. 3. The spiral spring 310 has a plurality of spring coils, which run around the longitudinal axis and are arranged over one another radially to the longitudinal axis. The inner end of the spiral spring 310 is fastened to a spring holding region 311 of the coupling shaft 230, which region can be seen in FIG. 12C. The outer end of the spiral spring 310 is mounted on a spring sleeve 320, which is held so as to be locked against relative rotation in the stop sleeve 240.

A coupling disc 270 is mounted on the coupling shaft 230, and is secured against rotation and displacement by a pin 271 in the transverse bore 232 of the coupling shaft 230. The coupling disc 270 has a plurality of longitudinal ribs on its outer peripheral surface. In the position of FIG. 3, these longitudinal ribs engage into the longitudinal grooves, which are complementary, on the inner side of the inner ring 250, but can be brought out of engagement by an axial displacement.

The dosing sleeve 60 has an axial passage opening, in which the push button 80 is arranged so as to be axially displaceable. The push button 80 is rotatable with a plurality of radially elastic arms 81 and is clicked on the proximal end 233 of the coupling shaft 230 so as to be secured against displacement. It abuts with its distal end against a proximal end face of the coupling disc 270. In the interior of the push button 80 there is a helical spring 82, which lies with its proximal end against the inner end face of the push button and presses with its distal end against a bearing ring 83. The bearing ring 83 has on its outer peripheral face longitudinal ribs, which are guided in corresponding longitudinal grooves in the inner covering surface of the push button 80. Thereby, the support ring 83 is arranged in the push button 80 so as to be locked against relative rotation and so as to be axially displaceable. The bearing ring 83 is configured be serrated in a flat manner on its distal end face. The proximal end face of the coupling disc 270 is formed so as to be serrated in a complementary manner hereto, so that the bearing ring 83 is axially meshed with the coupling disc 270. On distribution of the medicament, the coupling disc 270 rotates with respect to the bearing ring 83. Thereby, the serrated surfaces slide on one another, so that the toothing comes alternately into and out of engagement. Thereby, a characteristic clicking sound is produced, which indicates to the user that an administering is just taking place. The toothing of bearing ring 83 and coupling disc 270 may be configured so that each clicking corresponds to one unit, or of a predetermined multiple of one unit, of the administered medicament.

The mechanism for setting the dose and the distribution may be arranged and configured in the housing sleeve 20 so as to be protected against splashing, i.e., sealed. According to certain embodiments, four seals D1, D2, D3 and D4 may be provided. The seal D1 comprises a sealing ring, which lies in a sealing manner between the mechanism holder 150 and the bayonet sleeve 160. The mechanism holder 150 is mounted immovably and tightly in the housing 2, and the bayonet sleeve 160 is both displaceable and rotatable with respect to the mechanism holder 160 and is sealed with respect to the housing by the seal D1.

The seal D2 comprises a further sealing ring, constructed so as to be flat, which lies in a sealing manner between the bayonet sleeve 160 and the smooth outer side of the thrust sleeve 90. Thrust sleeve 90 may have a smooth (e.g., within accepted and/or manufacturing tolerances) or substantially smooth outer wall region, the length of which corresponds at least to the distance between the distal final position and the proximal initial position of its longitudinal movement, between which the thrust sleeve 90 is movable in the course of the administering. The sealing effect between seal D2 and thrust sleeve 90 may be facilitated by providing an outer wall region of the thrust sleeve 90 with fine structures, e.g. scales, a pattern or texture, in the range below 100 micrometers, e.g. below 10 micrometers, and may be configured as micro- or nano-structuring, at least along the length between the distal final position and the proximal initial position. A thrust sleeve 90 with such micro- or nano-structuring may be considered substantially smooth to one of skill in the art due to the minute size of the structures. However, one of skill in the relevant art would also appreciate the usefulness of such structures in maintaining and/or enhancing a seal between the thrust sleeve 90 and seal D2. In some embodiments, the outer wall region may extend from thrust flange 100 to guide cams 91. In addition, texture or structure provided on the substantially smooth surface may extend along the entire outer wall region or along portions thereof. Texture 93 along the thrust sleeve is depicted in FIG. 1B, which is configured as micro-structured scales. In addition or alternatively, other structures, such as surface protrusions or indentations, which may have a desired texture or structure, may be provided along the outer wall region. Such additional or alternative structures may have an orientation such that the structures are directed towards the proximal or distal direction. Furthermore, the thrust flange 100 is arranged tightly on the thrust sleeve 90. The region of the injection device, including the interior of the thrust sleeve 90, lying proximally from the bayonet sleeve 160, may thus be sealed against the region lying distally. Where fluids are introduced into this distal region, e.g., due to a breakage of the medicament carpule 40, the fluid may be prevented from penetrating into the mechanics, thus preventing contamination or jamming.

The other two seals are situated at the proximal end of the injection device. The seal D3 comprises a sealing ring, which lies in a sealing manner between the dosing sleeve 60 and the stop sleeve 240. The stop sleeve 240 is mounted immovably and tightly in the housing sleeve 20, whereas the dosing sleeve 60 is rotatable with respect to the stop sleeve 240. The seal D4 comprises a further sealing ring, which lies in a sealing manner between the dosing sleeve 60 and the push button 80. In addition, a transparent window covering 22 is placed in a fluid-tight manner on the window 21. Accordingly, mechanisms, operational components or mechanics, which are delimited toward the exterior by the housing sleeve 20, the dosing sleeve 60 and the push button 80, are also sealed toward the exterior and may be protected against the penetration of fluids. Rainfall or a glass of water accidentally spilt by the user can therefore also not harm the injection device.

The seal towards the thrust sleeve may be configured such that it acts as a stripper, similar to a windshield wiper in a car. For this, at least towards the distal side, there is as small a contact angle between the surfaces of the sealing element and the thrust sleeve, which may lie below 90 degrees.

Instead of conventional seals or in addition hereto, the parts which are to be sealed with respect to each other may be configured with a hydrophobic surface, such as being formed of or coated with a hydrophobic material. A hydrophobic surface may prevent the parts from being wetted. Drops of water thereby roll off and a leaking of fluids through gaps is efficiently prevented between the parts, which are to be sealed due to capillary effects. The parts provided with a hydrophobic surface, which are to be sealed with respect to each other, may therefore be arranged at a certain distance (gap) from each other, without the sealing effect being lost ("virtual seal").

A hydrophobic surface is understood here to mean a surface for which the contact angle of a water drop is at least 90 degrees, e.g., at least 110 degrees. The contact angle is the angle between the surface normal of the water drop and the respective surface at the contact site. Examples of materials with hydrophobic characteristics are PTFE (polytetrafluoroethylene) or PVDF (polyvinylidene fluoride), as well as other hydrophobic materials that may be formed as thin coatings, e.g., in the range of a few micrometers, to provide a hydrophobic surface.

In experiments, various pens and a sleeve were provided nanotechnologically with a hydrophobic coating. 20 pens with external diameters of 10.0 to 11.9 mm in graduations of 0.1 mm were examined. The pens were arranged centrally in a sleeve with 12 mm internal diameter, which corresponds to gap thicknesses of 0.05 mm to 1.0 mm in graduations of 0.05 mm. The interior of the sleeve was then acted upon with water. A sealing effect up to a gap thickness of approximately 0.5 mm was observed. With reciprocal rotation between pen and sleeve, a sealing effect up to a gap thickness of approximately 0.25 mm was observed.

To improve the sealing effect, the surfaces may be micro- or nano-structured, i.e., provided with structures, the dimensions of which are in the nanometer to micrometer range. These structures can have a selected direction, to inhibit the flow of fluids on the surface in one direction. Thus, for example, scales can be provided.

Figure 16:
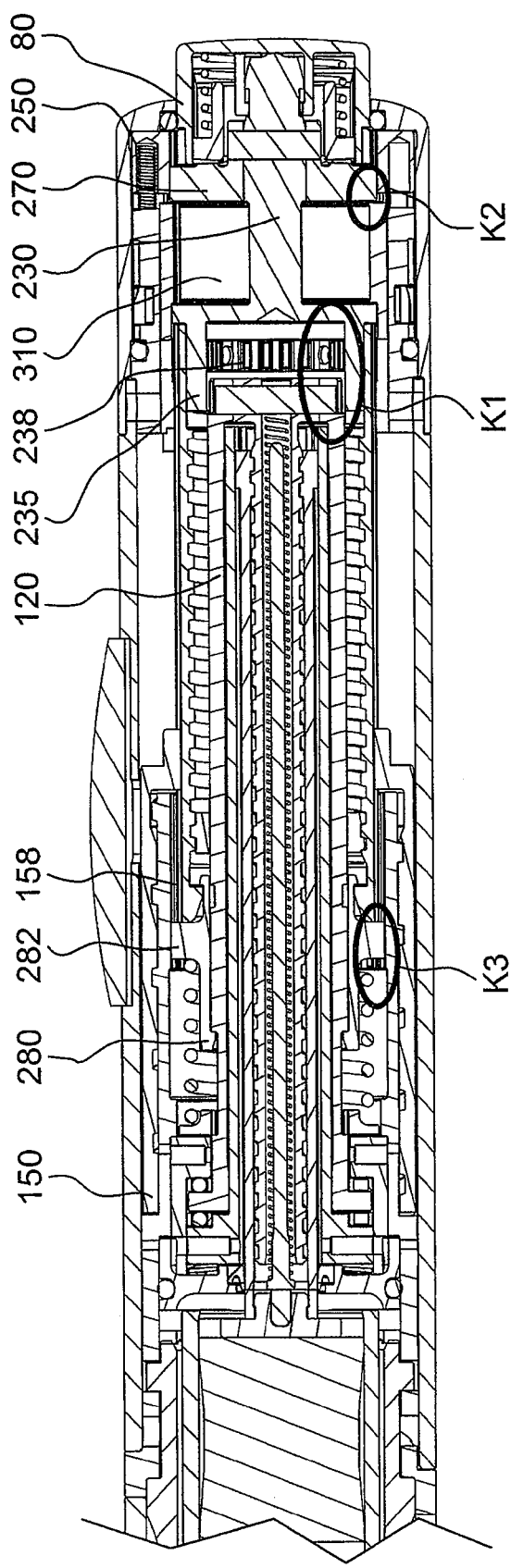
FIG. 16 is a longitudinal section through the injection device of FIG. 1A in the initial position.

The mode of operation of the injection device is now to be described below with reference to FIG. 16, in which an exemplary injection device is illustrated in its initial position before the first use. The mechanism described above for setting and distributing a dose has three couplings K1, K2 and K3 for the transmission of torques. Each of these couplings may be brought into and out of engagement by an axial movement of two components with respect to each other.

The coupling K1 is formed by the longitudinal grooves on the inner surface of the axial flange 235 of the coupling shaft 230 as a coupling input member in cooperation with the longitudinal ribs 122 on the outer side of the coupling sleeve 120 (cf. FIG. 5) as coupling output member. In the position of FIG. 16, this coupling is uncoupled, i.e., the coupling formed by the cooperation of the longitudinal grooves and longitudinal ribs is out of engagement. The coupling K1 can be coupled by an axial displacement of the coupling shaft 230 in the distal direction.

The coupling K2 is formed by the longitudinal grooves in the radial inner surface of the inner ring 250 as a coupling input member in cooperation with the longitudinal ribs on the radial outer surface of the coupling disc 270 as coupling output member. In the position of FIG. 16, this coupling is coupled, i.e., the toothing formed by the longitudinal grooves and longitudinal ribs is in engagement. The coupling K2 can be uncoupled by an axial displacement of the coupling disc 270 in the distal direction.

The coupling K3 is formed by the longitudinal ribs on the outer side of the outer ring flange arms 282 of the arresting sleeve 280 as coupling input member in cooperation with the longitudinal grooves 158 on the inner surface of the mechanism holder 150 as coupling output member. In the position of FIG. 13, this coupling is coupled. It can be uncoupled by an axial displacement of the arresting sleeve 280 in the distal direction.

All three couplings K1, K2 and K3 can be coupled and respectively uncoupled by the push button 80 being displaced axially. On pressing in of the push button 80, the coupling disc 270 and the coupling shaft 230, which is securely connected therewith, are displaced in the distal direction. In this instance, the coupling K1 comes into engagement, i.e., the coupling shaft is coupled for torque transmission with the coupling sleeve 120. At the same time, the coupling shaft 230 advances the transmission sleeve 210 in the distal direction. This entrains the arresting sleeve 280 in the distal direction, whereby the coupling spring 290 is compressed. When the coupling K1 arrives in engagement for the first time, the arresting sleeve 280 is not yet advanced sufficiently far to arrive with its outer ring flange arms 282 out of engagement with the mechanism holder 250. The coupling K3 is therefore initially still coupled. The same applies to the coupling K2: The coupling disc 270 is still in engagement with the inner ring 250. Therefore, all three couplings are coupled. When the push button 80 is pushed in further, the coupling K2 comes out of engagement. With a still further pushing in, coupling K3 comes out of engagement. Therefore, the couplings are as follows: Initial state: K1 uncoupled, K2 and K3 coupled. Pushing in of the push button 80: K1 couples, thereafter K2 uncouples, thereafter K3 uncouples.

Figure 19:
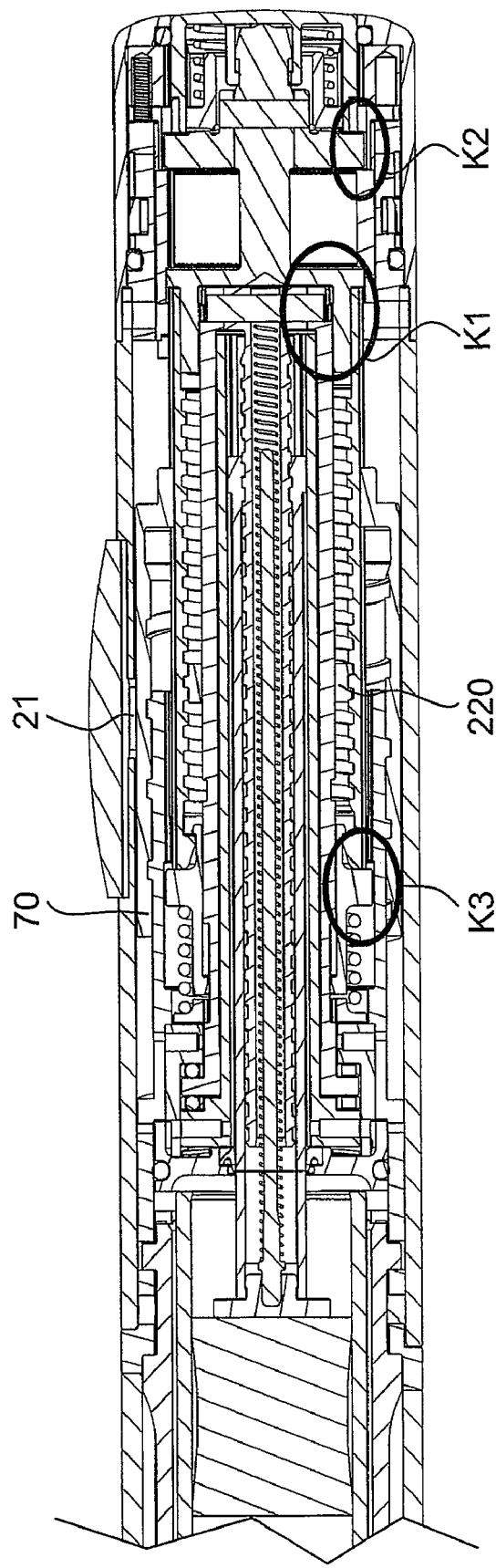
FIG. 19 is the longitudinal section of FIG. 16 after a first triggering and a second increase of dose.

FIG. 19, described further below, shows the injection device with the push button 80 pushed in completely. The coupling K1 is coupled, whereas the couplings K2 and K3 are uncoupled.

On releasing of the push button 80, the engaging of the couplings into each other runs in the reverse sequence. Here, the coupling spring 290 presses the arresting sleeve 280, the transmission sleeve 210, the coupling shaft 230, the coupling disc 270 and the push button 80 back into the distal initial position.

The couplings K1, K2 and K3 and the ratchet connection make possible the systematic transmission of torques between five functionally independent units. A first unit comprises the housing sleeve 20, the mechanism holder 150, the stop sleeve 240 and the spring ring 320. This unit can be regarded functionally as a holding arrangement or as a housing in an extended sense. It constitutes the stationary reference system for all movements.

A second unit comprises the dosing sleeve 60, the inner ring 250 and the ratchet ring 260. It can be regarded functionally as a rotatable dosing arrangement. This dosing arrangement is held detachably on the housing by the ratchet connection, but so as to be secure with regard to torque up to a certain value.

A third unit comprises the coupling disc 270, the coupling shaft 230 and the transmission sleeve 210, which are rigidly connected with each other, and by the spiral spring 310, connected therewith, which acts as the actual drive element. This unit can be regarded as a drive arrangement. The rotary movement of the drive arrangement is limited by two limiting elements, which are both guided on the transmission arrangement. The first limiting element is formed by the display drum 70, which limits the range of movement of the drive arrangement in both directions, a dosing direction and a correction and distribution direction. The second limiting element is formed by the dose limiting ring 220, which limits the range of movement of the drive arrangement at least in one direction, the dosing direction, independently of the first limiting element. The drive arrangement is able to be coupled detachably by the coupling K2 so as to be locked against relative rotation with respect to the dosing arrangement, which makes it possible to tension the drive element in the form of the spiral spring 310.

A fourth unit comprises the coupling sleeve 120 and the threaded rod 180, which form a rigid unit, the elements on which these parts are mounted, namely the guide sleeve 110, the bearing holder 130 and the ball bearing rings 140, and also the thrust sleeve 90. This unit constitutes a delivery arrangement, which converts a rotary movement of an input member in the form of the coupling sleeve 120 into a thrust of the delivery element in the form of the thrust sleeve 90. Its input member is able to be detachably coupled by the coupling K1 so as to be locked against relative rotation with the drive arrangement. In addition, it is able to be detachably coupled via the coupling K3 so as to be locked against relative rotation with the holding arrangement (i.e., the housing).

Furthermore, a triggering arrangement is present, which comprises the push button 80 and serves for the operation of the couplings K1 to K3.

The injection device is operated as follows. Starting from the initial position of FIG. 16, a dose is set, which is to be administered. For this, the dosing sleeve 60 is turned clockwise. In so doing, the dosing sleeve entrains the coupling disc 270 and the coupling shaft 230 via the coupling K2, and the spiral spring 310 is wound up. The torque generated is held by the ratchet connection between the co-rotating ratchet ring 260 and the stationary stop sleeve 240. Through the rotation of the coupling shaft 230, the transmission sleeve 210 and the display drum 70, which is guided thereon, are also co-rotated. The display drum 70, threadably guided on the mechanism holder 150, is additionally displaced axially in the proximal direction, and therefore performs as a whole a screw motion in the proximal direction. Markings on the surface of the display drum 70 pass through under the window 21 and indicate the set dose. Furthermore, the dose limiting ring 220, threadably engaged with the interior of the transmission sleeve 210 and arranged, secured with regard to rotation, on the coupling sleeve 120, is displaced in the proximal direction.

Figure 17:
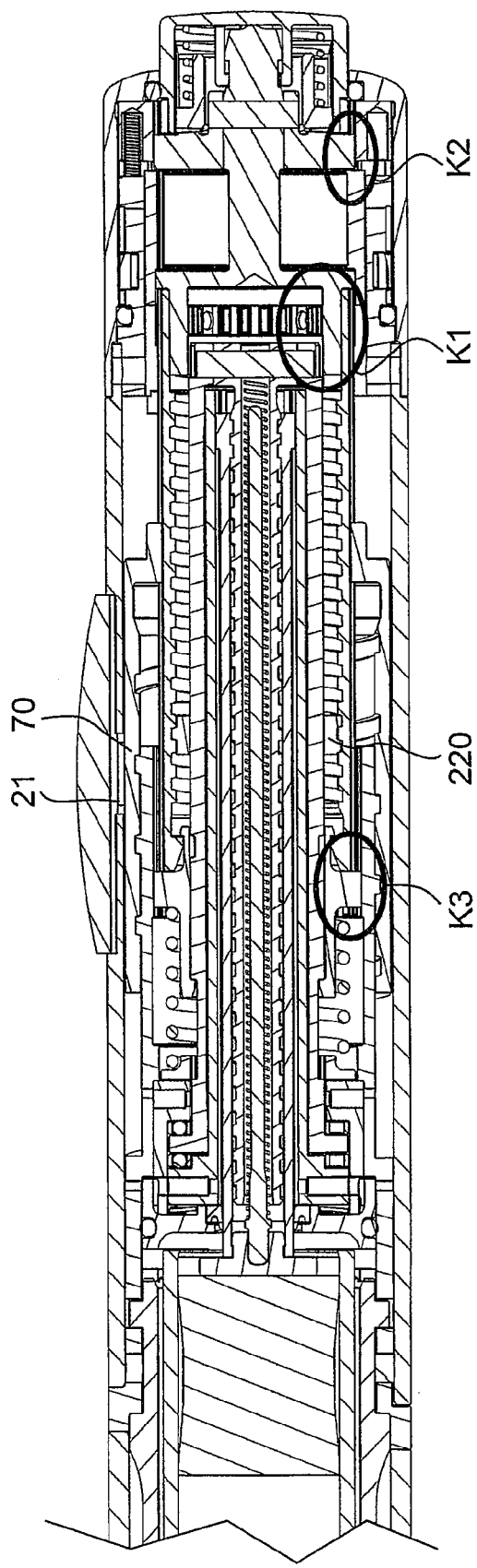
FIG. 17 is the longitudinal section of FIG. 16 after a first increase of dose up to half the maximum dose.

FIG. 17 shows the injection device after half the maximum individual dose has been set. The display drum has traveled rearwardly half-way between its distal (forward) and its proximal (rear) final position. In addition, the dose limiting ring 220 has traveled in the proximal direction by an amount proportional to the individual dose that has been set.

Figure 18:
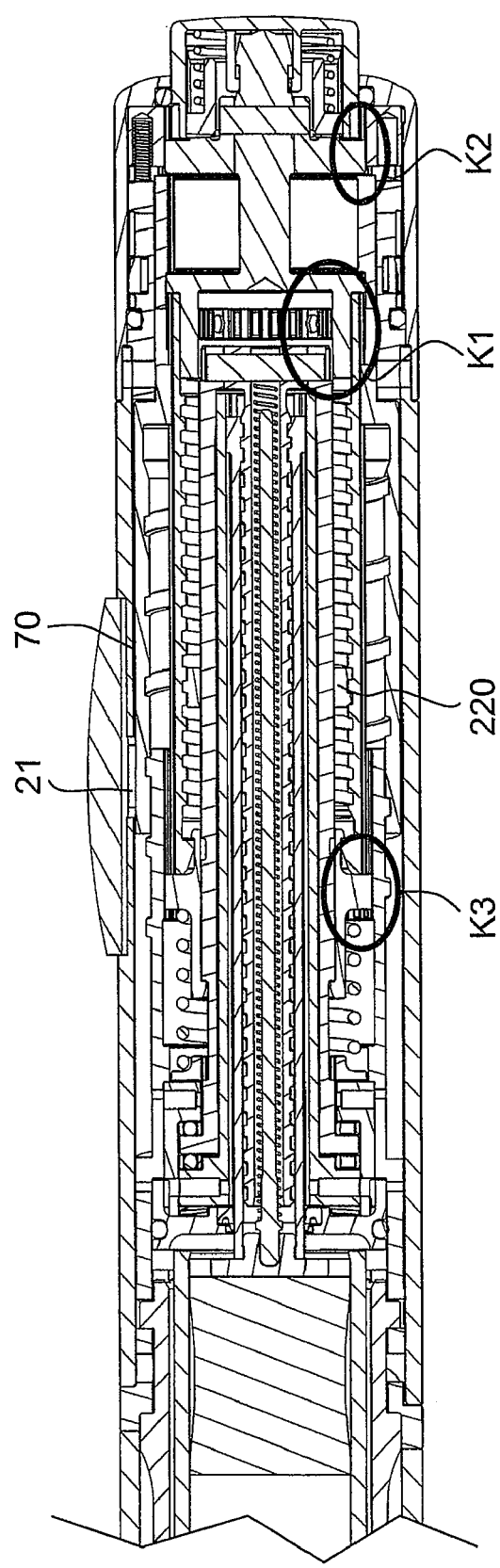
FIG. 18 is the longitudinal section of FIG. 16 after a first increase of dose up to the full maximum dose.

The rotation of the dosing sleeve 60 clockwise is limited, on the one hand, by the maximum movement range of the display drum 70, and on the other hand, by the maximum movement range of the dose limiting ring 220. After a predetermined number of revolutions of the dosing sleeve 60, the display drum 70 abuts with its proximal radial stop against the stop sleeve 240, in so far as the rotation of the dosing sleeve 60 has not been previously limited by the dose limiting ring 220, as is described further below. Thereby, no further rotation of the dosing sleeve 60 is possible. This position corresponds to the maximum individual dose, which can be set. This situation is illustrated in FIG. 18.

If the set dose is to be corrected, i.e., reduced, then the dosing sleeve 60 can be turned back anticlockwise against the force of the ratchet connection. As the ratchet connection in this direction absorbs the torque of the spiral spring 310, the ratchet connection is configured asymmetrically: The toothing on the end face has a larger angle of inclination on the side which is stressed by a torque which acts anticlockwise onto the dosing sleeve than on the side which is stressed with a torque clockwise (cf. the configuration of the teeth 244 in FIG. 14). The angle of inclination is understood here to mean the absolute amount of the angle between the respective flank of a tooth on the end face of the ratchet ring 260 or on the end face of the stop sleeve 240 and a cross-sectional area through the injector.

The distribution or delivery of the dose, which has been set is actuated or initated by the push button 80 being pushed in. In this instance, the coupling K1 is coupled, and a connection is produced which is locked against relative rotation between the coupling shaft 230, on the one hand, and the coupling sleeve 120 and also the threaded rod 180 rigidly connected therewith, on the other hand. All three couplings K1, K2 and K3 are coupled. On further pushing in of the push button 80, the coupling K2 uncouples. Thereby, the connection, which is locked against relative rotation between the dosing sleeve 60, on the one hand, and the coupling shaft 230 with the coupled coupling sleeve 120 and threaded rod 180, on the other hand, is cancelled. This leads to the ratchet connection no longer absorbing the torque of the spiral spring 310. However, the system is held so as to be locked against relative rotation via the coupling K2 in the mechanism holder 150 and hence in the housing sleeve 20. When the push button 80 is pressed further, the coupling K3 also uncouples. At this moment, the torque of the spiral spring 310 becomes free and acts via the coupling shaft 230 and the coupling sleeve 120 on the threaded rod 190. Hereby, these parts are set in an anticlockwise rotation. Through its thread engagement with the threaded rod 190, the thrust sleeve 90 undergoes an axial displacement in the distal direction. Via the thrust flange 100, the thrust sleeve advances the stopper 41 in the carpule 40. In this way, the medicament is distributed or injected.

During the distribution or injection process, axial forces act on the thrust sleeve 90: The torque of the spiral spring 310 is converted into a force in the thrust direction, which advances the stopper 41 in the carpule 40. These forces are absorbed by the ball bearings between the coupling sleeve 12 and the guide sleeve 110 and the bearing holder 130, in a low-friction manner, so that counter forces (i.e., frictional counter forces), which could reduce the driving torque, are minimized.

In the distribution, the display drum 70 is entrained by the rotation of the transmission sleeve 210 anticlockwise and is moved in the distal direction due to its engagement with the stationary mechanism holder 150, until it assumes its distal initial position. In this position, it is prevented from rotating further by a radial stop, whereby the distribution is terminated. After the end of the distribution, the display drum 70 indicates the dose "zero".

The distribution can be interrupted at any time by the push button 80 being released. Thereby, the couplings K3 and K2 couple again, and the coupling K1 uncouples again. The display drum 70 indicates the remaining residual dose which is further distributed when the push button is pressed again and thereby the distribution is continued.

The dose limiting ring 220 maintains its axial position during the distribution, because the transmission sleeve 210 and the coupling sleeve 120, between which the dose limiting ring 220 is situated, rotate synchronically.

After the end of the distribution, the injection device is ready for the next injection process. Compared with FIG. 16, however, two components have changed their position: On the one hand, the thrust sleeve 90 has traveled in accordance with the distributed dose in the distal direction. On the other hand, the dose limiting ring 220 has likewise traveled by an amount proportional thereto in the proximal direction. Apart from this, the state after the end of the injection corresponds to the initial state of FIG. 16. With each further injection, the thrust sleeve 90 therefore travels further in the distal direction, whereas the dose limiting ring 220 travels in the proximal direction. This is illustrated in FIG. 19, which illustrates the injection device after a first dose is administered, which corresponds to half the maximum individual dose, and then with the dosing sleeve a dose was again set, which in turn corresponds to half the maximum individual dose. The display drum indicates, as in FIG. 15, half the maximum individual dose, whereas the dose limiting ring 220 assumes a position in the transmission sleeve 210, which corresponds to the sum of the doses which have been set, e.g., twice half the maximum individual dose.

Figure 20:
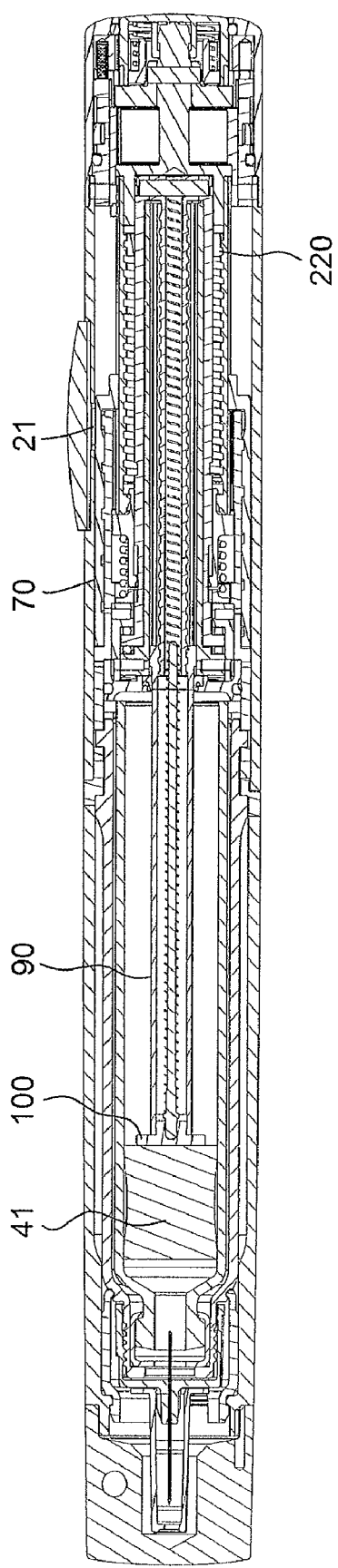
FIG. 20 is a longitudinal section through the injection device of FIG. 1A after a complete emptying of the carpule.

The maximum axial path by which the dose limiting ring 220 can travel in the proximal direction in the transmission sleeve corresponds to the content of a completely filled carpule. As soon as the sum of the doses set on the dosing sleeve corresponds to the carpule content, the dose limiting ring 220 reaches its proximal final position and abuts with its radial stop against the axial ring flange 235 of the coupling shaft 230, as is illustrated in FIG. 12A. Thereby, the dosing sleeve 60 is prevented from a further clockwise rotation, and no larger dose can be set than the dose corresponding to the remaining residual amount of the medicament in the carpule. FIG. 20 shows this situation, in which no further increasing of the dose is possible, although the display drum is situated in the distal initial position, i.e., the zero position. Correspondingly, the thrust sleeve 90 has reached its maximum, distal final position.

To exchange the carpule, the carpule sleeve 30 is detached from the mechanism holder 150 against the elastic resistance of the bayonet spring 170, and is unscrewed, guided through the corresponding guide slit 156 in the mechanism holder. Compulsorily, the bayonet sleeve 160 is twisted along its own, parallel guide slit 155, and is displaced in the distal direction. The guide sleeve 110 is drawn in the distal direction, and the movable parts, which are connected axially therewith, also travel in the distal direction, including the coupling sleeve 120, the threaded rod 190, the arresting sleeve 280, the transmission sleeve 210, the coupling shaft 230, the coupling disc 270 and the push button 80. The push button 80 is therefore drawn into the dosing sleeve 60 and thus indicates that the injection device is not ready for operation.

Through this axial displacement of the various parts of the mechanism, the couplings K2 and K3 come out of engagement, while K1 is already out of engagement. If a dose had still been set before the carpule change, but had not been administered, the wound spiral spring 310 sets the coupling shaft 230 and the transmission sleeve 210 connected therewith into an anticlockwise rotation, until the display drum 70 has reached its distal final position and prevents a further turning back by its radial stop on the mechanism holder 150. In this way, the display drum 70 is brought back into its distal initial position, the zero position. An automatic resetting of the dose display to zero therefore takes place.

If, before the carpule change, a residual amount of the medicament was still situated in the carpule 40, then the thrust sleeve 90 had not yet moved out to a maximum before the carpule change, and had therefore not yet reached its distal final position. On removal of the carpule sleeve 30, the helical spring 190 presses the guide needle 200, the thrust flange 100 and the thrust sleeve 90 in the distal direction. Thus, the threaded rod 180 is set in rotation via its screw connection with the interior of the thrust sleeve 90. The threaded rod 180 entrains the coupling sleeve 120 and the dose limiting ring 220. With this rotation, the dose limiting ring 220 is displaced into its proximal final position through its thread engagement with the transmission sleeve 210. As soon as the dose limiting ring 220 has reached this initial position, it prevents a further rotation of the coupling sleeve 120 and of the threaded rod 180, so that no further moving out of the thrust sleeve 90 is possible, and the thrust sleeve 90 has reached its distal final position, as illustrated in FIG. 1A. In addition, the display drum 70 is situated in the zero position, the dose limiting ring 220 in the proximal final position and the thrust sleeve 90 in its distal final position.

A new carpule 40 may be pushed into the carpule sleeve 30, and the carpule sleeve 30 with the carpule 40 held therein may be guided axially in the proximal direction against the housing sleeve 20. In this position, the stopper 41 of the carpule presses the thrust flange 100 and the thrust sleeve 90 against the force of the helical spring 190 in the proximal direction. As a result, the threaded rod 180 is set in rotation. The threaded rod entrains the coupling sleeve 120 and the dose limiting ring 220. The dose limiting ring, threadably engaged with the transmission sleeve 210, is displaced in the distal direction, i.e., in the direction of its initial position. The degree of displacement in this direction corresponds to the dose present in the carpule 40. With a completely filled carpule, the dose limiting ring 220 travels into its distal initial position. The carpule sleeve 30 is then pushed into the mechanism holder 150, with the radial pins 36 of the carpule sleeve 30 engaging again into the guide slits 156 in the mechanism holder 150 (cf. FIGS. 1 and 3). Through the positive guidance of the carpule sleeve 30 on insertion into the mechanism holder 150, the bayonet sleeve 160 is forced to follow the movement of the carpule sleeve 30 in the corresponding guide slits. The bayonet sleeve 160 is thereby brought back into its proximal final position, in which it is detachably locked by the bayonet disc 170 (cf. FIGS. 8 to 10). The injection device is thus situated in the initial position of FIG. 16 and, after the screwing of a new needle holder 31, is available for a new sequence of administrations.

Figure 21:
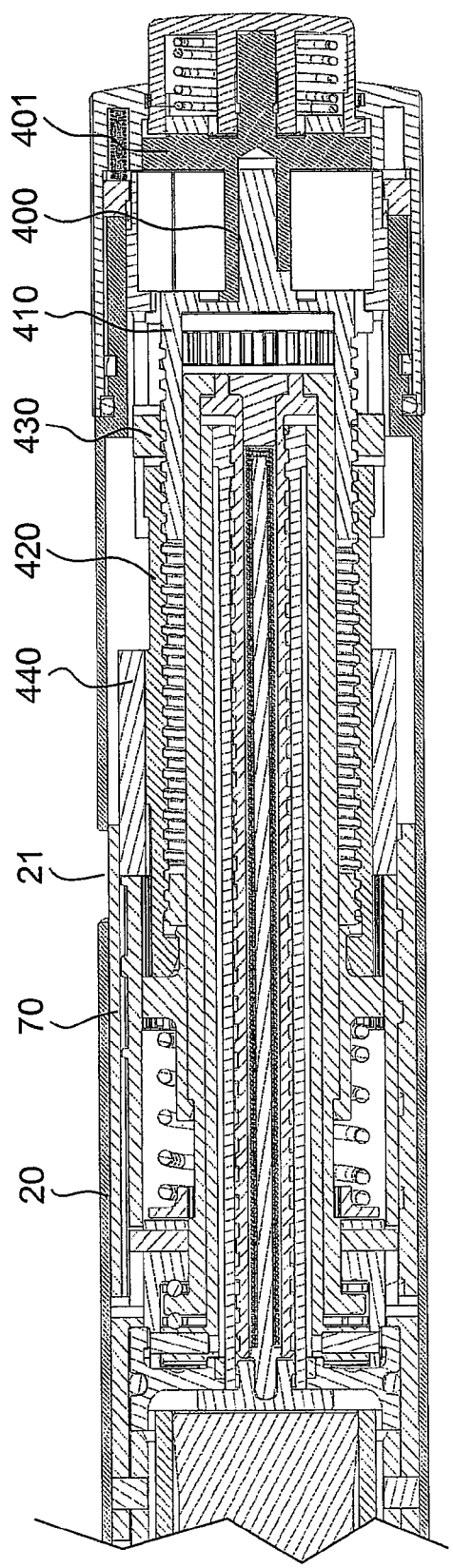
FIG. 21 is a longitudinal section through an injection device according to another embodiment.

In FIG. 21, another exemplary embodiment of an injection device according to the present invention is illustrated as a variant. The mode of operation is substantially the same as in the first embodiment described above. Parts which perform similarly are therefore designated by the same reference numbers as in the first embodiment, the differences of the second embodiment being described below.

In the second embodiment, the stop sleeve 240 is omitted. Rather, its function is taken over by the correspondingly extended housing sleeve 20.

The drive arrangement which, in the first embodiment, apart from the spiral spring 310, is formed from the coupling disc 270, coupling shaft 230 and transmission sleeve 210, is formed in the second embodiment by different parts, including a connecting shaft 400 (with coupling disc 401 formed integrally thereon), a first transmission sleeve 410 closed at the proximal end, and a second transmission sleeve 420 adjoining distally thereto. These three parts are, in turn, connected rigidly with each other.

Whereas in the first embodiment, the display drum served to indicate the set dose and to delimit the maximum individual dose which was able to be set in the dosing direction and to delimit the movement in the distribution direction, the latter function in the second embodiment is taken over by a second dose limiting ring 430. The latter is guided so as to be locked against relative rotation, but axially displaceable, in the housing sleeve 20. With an internal thread it runs on a corresponding external thread of the first transmission sleeve 410. Its axial movement is limited by two radial stops between a distal initial position, which corresponds to the zero position, and a proximal final position, which corresponds to the maximum dose which is able to be set. In this way, it takes over the stop functions of the display drum according to the first embodiment.

The display drum 70 in the second embodiment is guided axially displaceably via a carrier sleeve 440, rigidly connected therewith, and so as to be locked against relative rotation on the second transmission sleeve 420. Its mode of operation is otherwise identical to the first embodiment.

Apart from these differences, the structure and mode of operation of the injection device are substantially the same as in the first embodiment.

The differences between the first and the second embodiment show that the functions of an injection device according to the present invention can be reached in a variety of ways and the invention is in no way restricted to the exemplary embodiments. Various further modifications are possible, which may be due to manufacturing requirements.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for the administering of a fluid product, the device comprising:
   a housing;
   a delivery arrangement for delivering the product from a reservoir, wherein the delivery arrangement comprises a rotatable input member and a delivery element movable along a thrust axis, which delivery element is driven by a rotation of the input member;
   a drive arrangement coupled to the input member such that a rotation of the drive arrangement drives rotation of the input member about the thrust axis relative to the housing, wherein the drive arrangement is tensioned by a rotary tension movement;
   a rotatable dosing arrangement for setting a dose of the product, the rotatable dosing arrangement coupled to the drive arrangement such that rotation of the dosing arrangement tensions the drive arrangement; and
   a triggering arrangement movable from a position of rest into a triggering position to trigger an administering; wherein
   a first coupling is between the drive arrangement and the input member of the delivery arrangement, whereby the drive arrangement and the input member of the delivery arrangement are connected with each other to be locked against relative rotation in a coupled position and are detached from each other in an uncoupled position, wherein
   a second coupling is between the dosing arrangement and the drive arrangement, whereby the dosing arrangement and the drive arrangement are connected with each other to be locked against relative rotation in a coupled position and are detached from each other in an uncoupled position, and wherein
   in the position of rest of the triggering arrangement the first coupling assumes its uncoupled position and the second coupling assumes its coupled position, so that a rotation of the dosing arrangement is able to be transferred to the drive arrangement and not to the delivery arrangement, and a movement of the triggering arrangement from the position of rest into the triggering position firstly brings about a coupling of the first coupling and thereafter an uncoupling of the second coupling, so that the drive arrangement is released and the resulting drive movement is able to be transferred to the delivery arrangement.

2. The device according to claim 1, wherein the dosing arrangement is able to be fixed detachably to be secure with regard to torque with respect to the housing.

3. The device according to claim 2, wherein the dosing arrangement is able to be fixed detachably by a ratchet connection to be secure with regard to torque with respect to the housing.

4. The device according to claim 3, wherein the ratchet connection is constructed as a double slip coupling which makes possible a manual turning of the dosing arrangement relative to the housing both in a first direction of rotation to increase the dose to be administered and in an opposite direction of rotation to reduce the dose.

5. The device according to claim 4, wherein the ratchet connection comprises a spring-loaded toothing, wherein the toothing is asymmetrical.

6. The device according to claim 5, wherein the ratchet connection comprises two ratchet elements axially opposite each other, on the end faces of which are teeth.

7. The device according to claim 6, wherein a first of the ratchet elements is a spring-loaded ratchet ring movable axially in the direction of the second ratchet element, which ratchet ring is arranged to be locked against relative rotation with respect to the dosing element, and wherein the second ratchet element is connected to be locked against rotation and displacement with respect to the housing.

8. The device according to claim 7, wherein the ratchet ring is spring-loaded by a plurality of springs arranged along the periphery of the ratchet ring.

9. A device for the administering of a fluid product, the device comprising:
   a housing;
   a delivery arrangement for delivering the product from a reservoir, wherein the delivery arrangement comprises a rotatable input member and a delivery element movable along a thrust axis, which delivery element is driven by a rotation of the input member;
   a drive arrangement for producing a rotary drive movement about the thrust axis relative to the housing, the drive arrangement comprising a spiral spring that is tensioned by a rotary tension movement;
   a rotatable dosing arrangement for setting a dose of the product and for tensioning the drive arrangement; and
   a triggering arrangement movable from a position of rest into a triggering position to trigger an administering; wherein
   a first coupling is between the drive arrangement and the input member of the delivery arrangement, whereby the drive arrangement and the input member of the delivery arrangement are connected with each other to be locked against relative rotation in a coupled position and are detached from each other in an uncoupled position, wherein
   a second coupling is between the dosing arrangement and the drive arrangement, whereby the dosing arrangement and the drive arrangement are connected with each other to be locked against relative rotation in a coupled position and are detached from each other in an uncoupled position, and wherein in the position of rest of the triggering arrangement the first coupling assumes its uncoupled position and the second coupling assumes its coupled position, so that a rotation of the dosing arrangement is able to be transferred to the drive arrangement and not to the delivery arrangement and a movement of the triggering arrangement from the position of rest into the triggering position firstly brings about a coupling of the first coupling and thereafter an uncoupling of the second coupling, so that the drive arrangement is released and the resulting drive movement is able to be transferred to the delivery arrangement.

10. The device according to claim 9, wherein the first coupling is formed by longitudinal grooves on an inner surface of an element of the drive arrangement and longitudinal ribs on an outer surface of an element locked against relative rotation with respect to the input member of the delivery arrangement, and wherein the second coupling is formed by longitudinal grooves on an inner surface of an element of the dosing arrangement and longitudinal grooves on an outer surface of an element of the drive arrangement.

11. A device for the administering of a fluid product, the device comprising:
a housing;
a delivery arrangement for delivering the product from a reservoir, wherein the delivery arrangement comprises a rotatable input member and a delivery element movable along a thrust axis, which delivery element is driven by a rotation of the input member;
a drive arrangement coupled to the input member such that a rotation of the drive arrangement drives a rotation of the input member about the thrust axis relative to the housing, the drive arrangement comprising a spiral spring that is tensioned by a rotary tension movement;
a rotatable dosing arrangement for setting a dose of the product the rotatable dosing arrangement coupled to the drive arrangement such that rotation of the dosing arrangement tensions the drive arrangement; and
a triggering arrangement movable from a position of rest into a triggering position to trigger an administering, the triggering arrangement comprising a push button disposed on a proximal end of the housing; wherein
a first coupling is between the drive arrangement and the input member of the delivery arrangement, whereby the drive arrangement and the input member of the delivery arrangement are connected with each other to be locked against relative rotation in a coupled position and are detached from each other in an uncoupled position, wherein a second coupling is between the dosing arrangement and the drive arrangement, whereby the dosing arrangement and the drive arrangement are connected with each other to be locked against relative rotation in a coupled position and are detached from each other in an uncoupled position, a third coupling is between the housing and the delivery arrangement, wherein the housing and the delivery arrangement are connected with each other and locked against relative rotation in a coupled position and are detached from each other in an uncoupled position, and wherein in the position of rest of the triggering arrangement the first coupling assumes its uncoupled position and the second and third couplings assume their coupled position, so that a rotation of the dosing arrangement is able to be transferred to the drive arrangement and not to the delivery arrangement, and a movement of the triggering arrangement from the position of rest into the triggering position firstly brings about a coupling of the first coupling, thereafter an uncoupling of the second coupling, and thereafter an uncoupling of the third coupling so that the drive arrangement is released and the resulting drive movement is able to be transferred to the delivery arrangement.

12. The device according to claim 11, wherein the third coupling is formed by longitudinal ribs on an outer side of an element locked against relative rotation with respect to the input member of the delivery arrangement, and longitudinal grooves on an inner side of an element locked against relative rotation with respect to the housing.

13. The device according to claim 12, wherein the triggering arrangement is movable between the position of rest and the triggering position in a distal direction along the thrust axis, and wherein each of the couplings comprises a coupling input member and a coupling output member, which through a movement of the triggering arrangement undergo a relative displacement with respect to each other and are thereby able to be brought into and out of engagement.

14. The device according to claim 13, wherein each of the couplings is formed by longitudinal grooves and longitudinal ribs on radial inner or outer surfaces of the respective coupling input member or coupling output member.

15. The device according to claim 14, wherein the drive arrangement is displaceable along the thrust axis, so that a movement of the triggering arrangement from the position of rest to the triggering position brings about a displacement of the drive arrangement in a distal direction.

16. The device according to claim 15, wherein the drive arrangement is spring-loaded along the thrust axis in a proximal direction.

* * * * *

UNITED STATES PATENT AND TRADEMARK OFFICE
CERTIFICATE OF CORRECTION

PATENT NO. : 8,048,037 B2  
APPLICATION NO. : 12/403887  
DATED : November 1, 2011  
INVENTOR(S) : Philippe Kohlbrenner et al.

Page 1 of 1

It is certified that error appears in the above-identified patent and that said Letters Patent is hereby corrected as shown below:

ON THE TITLE PAGE | | | Should Read

Item 73 Assignee | "TecPharma Licensing AG, Brugdorf, Switzerland" | -- TecPharma Licensing AG, Burgdorf, Switzerland --

CLAIMS

| Column | Line | | Should Read |
|---|---|---|---|
| 27 | 8-9 | "delivery arrangement and" | -- delivery arrangement, and -- |

Signed and Sealed this  
Tenth Day of April, 2012

David J. Kappos  
*Director of the United States Patent and Trademark Office*